(12) United States Patent
Kovanyine Lax et al.

(10) Patent No.: US 9,133,132 B2
(45) Date of Patent: Sep. 15, 2015

(54) METHOD FOR THE PREPARATION OF HIGH-PURITY PHARMACEUTICAL INTERMEDIATES

(75) Inventors: Gyorgyi Kovanyine Lax, Budapest (HU); Gyula Simig, Budapest (HU); Balazs Volk, Budapest (HU); Ferenc Lorant Bartha, Tiszavasvari (HU); Gyorgy Krasznai, Budapest (HU); Gyorgy Ruzsics, Budapest (HU); Eva Sipos, Budapest (HU); Kalman Nagy, Budapest (HU); Gyorgy Morovjan, Budapest (HU); Jozsef Barkoczy, Budapest (HU); Adrienn Keszthelyi, Budapest (HU); Janos Imre, Budapest (HU); Gabor Bagyinszki, Godollo (HU)

(73) Assignee: EGIS GYOGYSZERGYAR NYILVANOSAN MUKODO RESZVENYTARSASAG, Budapest (HU)

(*) Notice: Subject to any disclaimer, the term of this patent is extended or adjusted under 35 U.S.C. 154(b) by 0 days.

(21) Appl. No.: 13/990,283

(22) PCT Filed: Nov. 29, 2011

(86) PCT No.: PCT/HU2011/000113
§ 371 (c)(1),
(2), (4) Date: Aug. 28, 2013

(87) PCT Pub. No.: WO2012/073055
PCT Pub. Date: Jun. 7, 2012

(65) Prior Publication Data
US 2013/0338360 A1    Dec. 19, 2013

(30) Foreign Application Priority Data

Nov. 29, 2010  (HU) .................................... 1000637

(51) Int. Cl.
*C07D 239/42*    (2006.01)
*A61K 31/505*    (2006.01)

(52) U.S. Cl.
CPC ............ *C07D 239/42* (2013.01); *A61K 31/505* (2013.01)

(58) Field of Classification Search
CPC ..................................................... C07D 239/42
See application file for complete search history.

(56) References Cited

U.S. PATENT DOCUMENTS

| 8,309,719 B2 | 11/2012 | Bastarda et al. |
| 8,404,841 B2 | 3/2013 | Reddy et al. |
| 2007/0255060 A1 | 11/2007 | Okada et al. |
| 2009/0011839 A1 | 4/2009 | Zilcar et al. |
| 2009/0275752 A1 | 11/2009 | Reddy et al. |
| 2010/0056783 A1 | 3/2010 | Satyanarayana Reddy et al. |
| 2010/0069635 A1 | 3/2010 | Bollikonda et al. |
| 2011/0184172 A1 | 7/2011 | Bastarda et al. |
| 2011/0301348 A1 | 12/2011 | Okada et al. |
| 2012/0116082 A1 | 5/2012 | Kovanyin Lax et al. |

FOREIGN PATENT DOCUMENTS

| WO | WO-2005 042522 | 5/2005 | |
| WO | WO-2006 136407 | 12/2006 | |
| WO | WO-2007 125547 | 11/2007 | |
| WO | WO 2007/125547 | * 11/2007 | ........... C07D 215/14 |
| WO | WO-2008 015563 | 2/2008 | |
| WO | WO-2008 038132 | 4/2008 | |
| WO | WO-2008 044243 | 4/2008 | |
| WO | WO-2008 067440 | 6/2008 | |
| WO | WO-2009 019211 | 2/2009 | |
| WO | WO-2010 081861 | 7/2010 | |
| WO | WO-2010 082072 | 7/2010 | |
| WO | WO-2011 132172 | 10/2011 | |

OTHER PUBLICATIONS

International Search Report for PCT/HU2011/000113, Date of the actual completion of the international search: May 14, 2012, Date of mailing of the international search report: May 23, 2012.

* cited by examiner

*Primary Examiner* — Erich A Leeser
(74) *Attorney, Agent, or Firm* — Millen, White, Zelano & Branigan P.C.

(57) ABSTRACT

The present invention is related to intermediates useful in the preparation of pharmaceutically acceptable salts of (+)-7-[4-(4-fluorophenyl)-6-isopropyl-2-(methanesulfonyl-methyl-amino)-pyrimidin-5-yl]-(3R,5S)-dihydroxy-hept-6-enoic acid and polymorphs of said intermediates, methods for preparation thereof and use thereof.

26 Claims, 4 Drawing Sheets

Figure 1 Powder X-ray diffractogram of crystalline Form II rosuvastatin TBA salt [compound of the Formula(III)]

Figure 3 Powder X-ray diffractogram of crystalline Form II rosuvastatin methylester [compound of the Formula (IIa)]

METHOD FOR THE PREPARATION OF HIGH-PURITY PHARMACEUTICAL INTERMEDIATES

TECHNICAL FIELD OF THE INVENTION

The present invention is related to the preparation of intermediates useful in the manufacturing of (+)-7-[4-(4-fluorophenyl)-6-isopropyl-2-(methanesulfonyl-methyl-amino)-pyrimidin-5-yl]-(3R,5S)-dihydroxy-hept-6-enoic acid of the Formula (I)

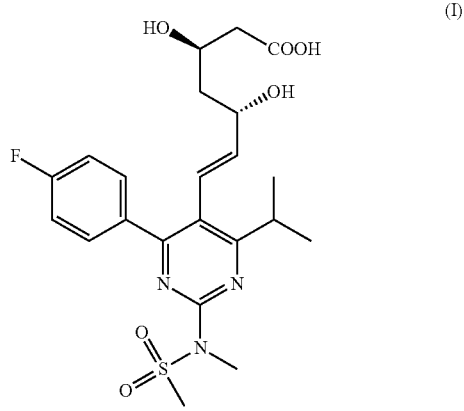

(I)

and pharmaceutically acceptable salts thereof, new, industrially advantageous modifications of the intermediates and use thereof.

(+)-7-[4-(4-fluorophenyl)-6-isopropyl-2-(methanesulfonyl-methyl-amino)-pyrimidin-5-yl]-(3R,5S)-dihydroxy-hept-6-enoic acid of the Formula (I) is a pharmaceutically active ingredient known under the International Nonproprietary Name rosuvastatin, which is effective in regulating the lipid metabolism. Rosuvastatin exerts its activity by inhibiting the enzyme 2-hydroxy-2-methyl-glutaryl-coenzim-A reductase present in the liver, thus reducing the rate of cholesterol biosynthesis and the cholesterol concentration of blood plasma. Rosuvastatin of the Formula (I)—especially in the form of salts—is used in the medicine for the treatment of hypercholesterolemia, hyperlipoproteinemia and atherosclerosis.

More specifically, the present invention is related to an industrially applicable method for the preparation of rosuvastatin tert-butylammonium (TBA) salt of the Formula (III)

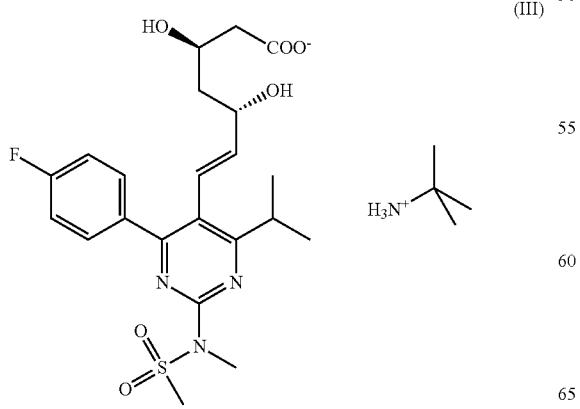

(III)

in high purity. According to the method of the present invention, rosuvastatin TBA salt of the Formula (III) is obtained by reacting tert-butylamine directly with a starting material selected from rosuvastatin methylester of the Formula (IIa), rosuvastatin ethylester of the Formula (IIb) or rosuvastatin t-butylester of the Formula (IIIc) in a suitable solvent. We have found that a particularly suitable starting material is a crystalline form of a rosuvastatin ester of the general Formula (II).

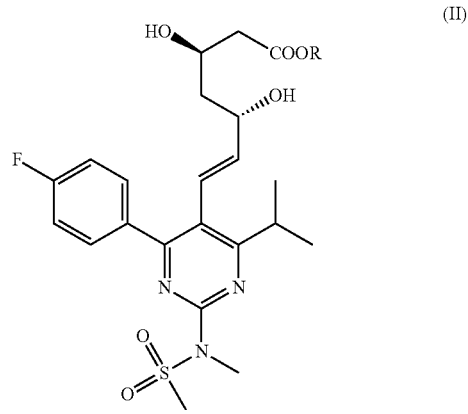

(II)

In the Formula (II), R represents methyl, ethyl or tert-butyl.

According to a further aspect of the present invention, there is provided a method for the preparation of new crystalline forms of rosuvastatain methylester of the Formula (IIa)

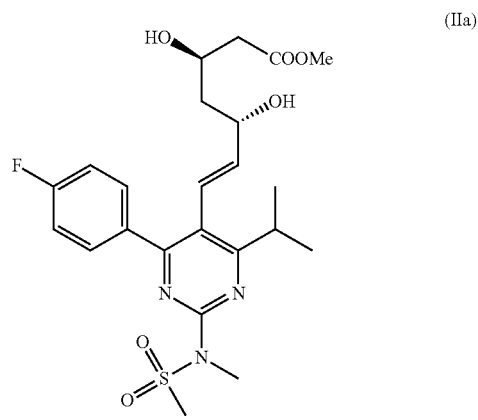 [SMILES: COC(=O)C[C@H](O)C[C@H](O)/C=C/c1c(-c2ccc(F)cc2)nc(N(C)S(C)(=O)=O)nc1C(C)C]

(IIa)

and rosuvastatin ethylester of the Formula (IIb)

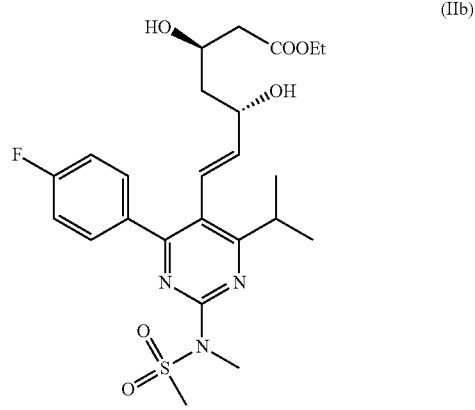 [SMILES: CCOC(=O)C[C@H](O)C[C@H](O)/C=C/c1c(-c2ccc(F)cc2)nc(N(C)S(C)(=O)=O)nc1C(C)C]

(IIb)

According to a still further aspect of the present invention, there are provided crystalline Form II and amorphous modifications of rosuvastatin TBA salt of the Formula (III), which are useful as reference substances during the analytical testing of the morphology of rosuvastatin TBA salt.

BACKGROUND ART (+)-7-[4-(4-fluorophenyl)-6-isopropyl-2-(methansulfonyl-methyl-amino)-pyrimidin-5-yl]-(3R,5S)-dihydroxy-hept-6-enoic acid (rosuvastatin) of the Formula (I) is a known compound which has been disclosed for the first time in European Patent No. 521471 in the form of the free acid and as certain pharmaceutically acceptable salts, e.g. rosuvastatin calcium salt of the Formula (IV)

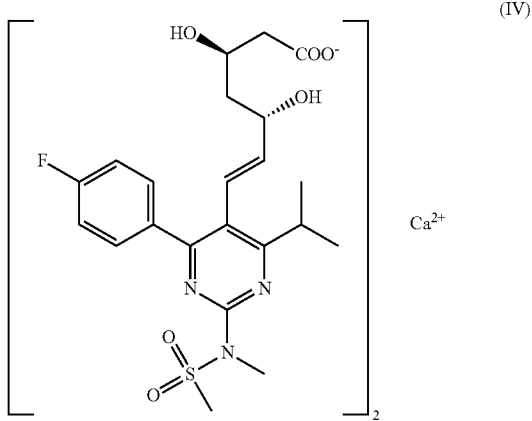

as well as ammonium salts thereof.

Rosuvastatin zinc (2:1) salt of the Formula (V)

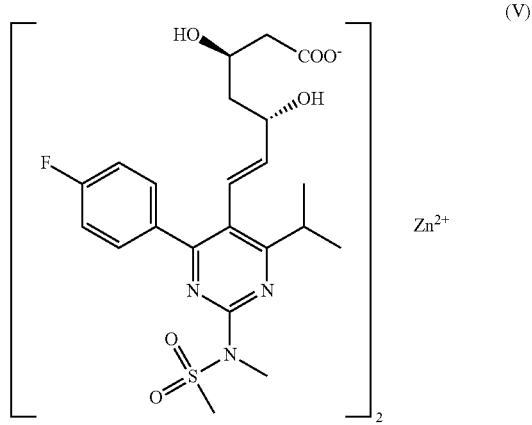

has been disclosed in Published Hungarian Patent Application P0600293 and in Published International Patent Application WO 2007119085.

According to the method of preparation disclosed in European Patent No. 521471, preparation of a rosuvastatin salt is carried out by saponifying a rosuvastatin ester of the general Formula (II) and if desired, the rosuvastatin salt thus obtained is transformed into rosuvastatin acid and either the directly obtained rosuvastatin salt or rosuvastatin free acid of the Formula (I) is transformed into a pharmaceutically acceptable salt, preferably into the calcium salt of the Formula (IV).

Rosuvastatin is an easily decomposing, light-sensitive compound, therefore further methods have been developed with the aim to obtain rosuvastatin in higher purity.

The chemical purity of pharmaceutically active ingredients is regulated by strict official norms issued by health authorities. Thus, according to the ICH Guidelines—even in the case of impurities with known chemical structure—the maximum limit concentration thereof is fixed at 0.1% in a pharmaceutically active ingredient.

Salts of rosuvastatin formed with amines are widely used during the manufacture of rosuvastatin salts used in the production of finished dosage forms. According to the state of the art, such salts of rosuvastatin formed with amines are transformed into a pharmaceutically acceptable alkali metal or alkali earth metal salts of rosuvastatin by setting the amine free from the salt using a stronger base and the thus obtained salt, which is usually an alkali metal salt, is subsequently transformed into the salt form used as active ingredient in the finished dosage form.

Published International Patent Application WO 01060804 is related to crystalline ammonium, methylammonium, ethylammonium, diethanolammonium, tris(hydroxymethyl)-methylammonium, benzylammonium or 4-methoxybenzyl-ammonium salts, which are transformed into amorphous rosuvastatin calcium salt by converting a rosuvastatin ammonium salt mentioned above into rosuvastatin sodium salt using aqueous sodium hydroxide solution, which is converted in the second step into rosuvastatin calcium (2:1) salt of the Formula (IV), and filtering the product from the aqueous solution. The purity of the product has not been disclosed.

Published International Patent Application WO 2008038132 discloses salts of rosuvastatin formed with diamines. Among the salts, only the dibenzylethylenediamine salt is characterized by X-ray diffraction data. The salts are prepared starting from rosuvastatin of the Formula (I) or rosuvastatin sodium salt.

Published International Patent Application WO 2008067440 discloses a method for the preparation of rosuvastatin calcium salt of the Formula (IV) starting from the dehydroabiethylamine salt of rosuvastatin through rosuvastatin sodium salt, in an aqueous solvent. The purity of the rosuvastatin calcium salt disclosed in an example is 99.80% as measured by high-performance liquid chromatography (HPLC) and contains the diastereomer impurity in 0.14% concentration, which is very close to the limit concentration (0.15%).

Direct transformation of several rosuvastatin ammonium salts into rosuvastatin calcium salt (wherein no rosuvastatin sodium salt is produced) has been disclosed in Published International Patent Applications WO 2004014872 and WO 2006136407. The reactions are carried out in an aqueous solvent.

Published International Patent Application WO 2004014872 is related to a method for preparation of rosuvastatin calcium salt with specific operating parameters, which results in the enhancement of the filtering efficiency during the isolation of the salt precipitating from water. In the method, rosuvastatin calcium salt of the Formula (IV) is obtained from certain water-soluble rosuvastatin ammonium salts (ammonium, tris-hydroxymethyl-methylammonium, methylammonium salts).

Published International Patent Application WO 2005077916 is related to crystalline and amorphous rosuvastatin cyclohexyl-, dicyclohexyl-, isopropyl-, diisopropyl- and (S)-1-methylbenzyl-ammonium salts. These salts are prepared by reacting a rosuvastatin ester, rosuvastatin or rosuvastatin lactone with the corresponding amine and purified by recrystallization. However, no method parameters have been disclosed or exemplified for the method using ester or lactone as starting materials, therefore neither the yield of the method nor the quality of the product can not be determined. The salts mentioned above are transformed into rosuvastatin calcium of the Formula (IV) by converting first the rosuvastatin ammonium salt into rosuvastatin lactone of the Formula (VI)

Application WO 2007000121, hydrolysis of rosuvastatin methylester of the Formula (IIa) is carried out using lithium hydroxide.

Saponification of Rosuvastatin Tert-Butylester of the Formula (IIc)

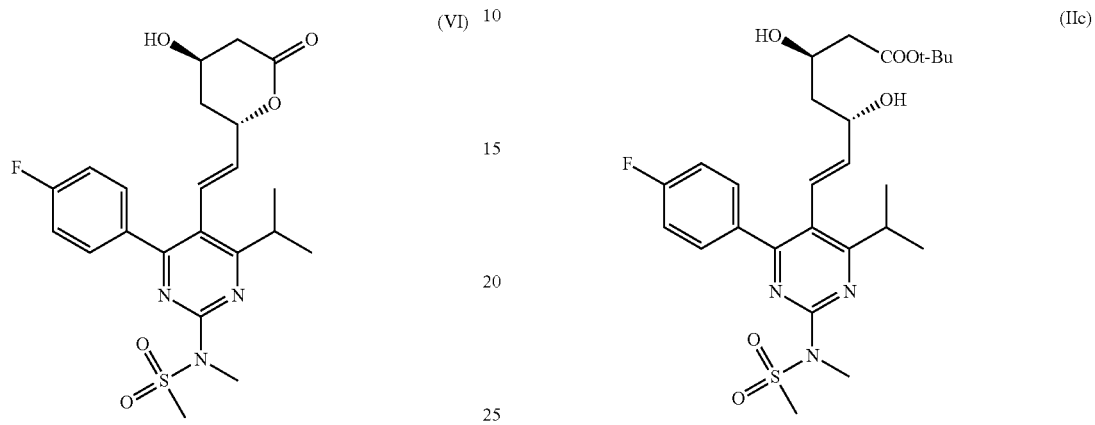

which is subsequently converted into the sodium salt and by reacting with a calcium ion source in aqueous medium and filtering, amorphous rosuvastatin calcium salt having its purity in excess of 99.5% (as determined by HPLC) is obtained. Nevertheless, the concentration of the diastereomeric impurity is high: using the method disclosed in the above-mentioned application, the concentration of the diastereomeric impurity can not be decreased below approx. 0.25%. Such an active ingredient, however, does not comply with internationally accepted ICH Guidelines, since the limit concentration for impurities having known chemical structure is thereby set to 0.1% for each impurity. A further disadvantage of the method is that the ammonium salt is transformed into the final product through further intermediates in multiple steps.

In Published International Patent Application WO 2005051921, a method for purification of rosuvastatin calcium salt through the crystalline isopropyl- or cyclohexylammonium salt has been disclosed. Rosuvastatin calcium salt is first transformed into rosuvastatin of the Formula (I), which is thereafter converted into rosuvastatin isopropyl- or cyclohexylammonium salt using ethylacetate as solvent. Subsequently the ammonium salt is transformed into sodium salt in aqueous medium and the sodium salt is transformed into rosuvastatin calcium salt (2:1) of the Formula (I) in an aqueous solvent. The yield of the reaction is 73.6% without disclosing the purity.

There are several methods in the state of the art relating to the hydrolysis of rosuvastatin esters with bases. In most cases, esters are saponified with aqueous alkali metal hydroxides yielding rosuvastatin alkali metal salts. Ammonium salts are prepared by converting a rosuvastatin alkali metal or alkali earth metal salt into rosuvastatin acid of the Formula (I) which is subsequently reacted with an amine yielding ammonium salt.

Thus, for example, hydrolysis of rosuvastatin methylester of the Formula (IIa) with aqueous sodium hydroxide solution has been disclosed in Published International Patent Applications WO 2003097614, WO 2004052867 and WO 2006017357. According to Published International Patent by sodium hydroxide has been disclosed in Published International Patent Applications WO 2006100689, WO 2006106526, WO 2007099561 and WO 2007125547. A method for the hydrolysis of rosuvastatin ethylester of the Formula (IIb) using sodium hydroxide has been disclosed in Published International Patent Application WO 2007000121.

In Published International Patent Application WO 2005023778, a method for preparation of rosuvastatin calcium salt starting from rosuvastatin alkylester has been described. The ester is hydrolyzed in an alcoholic solution with sodium-potassium- or barium-hydroxide, the solution is evaporated, the salt is dissolved in water, the aqueous solution is extracted with an organic solvent and after removing the organic solvent and adding a calcium source, the calcium salt is formed which is isolated by filtration. However, the method has been demonstrated by an example of saponifying rosuvastatin tert-butyltester of the Formula (IIc) with sodium hydroxide only.

According to Published International Patent Application WO 2006136408, amorphous rosuvastatin calcium salt can be prepared by hydrolyzing a rosuvastatin $C_1$-$C_5$ alkylester with a base in an aprotic solvent or in a mixture of an aprotic solvent and water. Thereafter a calcium salt is added to the reaction mixture and the amorphous rosuvastatin calcium salt is isolated. In the examples, sodium hydroxide is used as a base.

Crystalline forms of each rosuvastatin ethyl-isopropyl- and tert-butylester of rosuvastatin corresponding to Formulae (IIa), (IIb) and (IIc), respectively, have been disclosed in Published International Patent Application WO 2005042522. Crystalline modifications of the esters have been characterized by powder X-ray diffractograms. Crystalline rosuvastatin ethylester of the Formula (IIb) has been prepared by purifying the crude product on silica gel using a solvent mixture of toluene-hexane (1:1). The solution is filtered and evaporated. In the present specification, crystalline form of rosuvastatin ethylester of the Formula (IIb) prepared according to the method of the above-mentioned application is referred to as Form I rosuvastatin ethylester. Published International Patent Application WO 2009019211 discloses a crystalline modification of rosuvastatin methylester of the Formula (IIa) characterized by powder X-ray diffractogram.

In the present specification, this modification is referred to as Form I rosuvastatin methylester of the Formula (IIa). Crystalline Form I rosuvastatin methylester of the Formula (IIa) is prepared according to the state of the art by purifying crude methylester by preparative HPLC using diisopropylether-isopropanol (98.5:1.5) solvent mixture. The collected main fraction is concentrated by evaporation, subsequently crystallized at −20° C. for 3 days and filtered. The filtrate is evaporated to dryness, thus crystalline Form I rosuvastatin methylester of the Formula (IIa) is obtained.

Published International Patent Application WO 2006136407 is related to a method for preparation of amorphous rosuvastatin calcium, which comprises hydrolysing a rosuvastatin $C_1$-$C_5$ alkylester in the presence of an organic nitrogen base (an amine, quaternary ammonium hydroxide, amidine, guanidine etc.), in a mixture of water and an aprotic organic solvent. The salt formed with the corresponding nitrogen base thus obtained is transformed into rosuvastatin calcium salt by the addition of a calcium cation source. In the application, several rosuvastatin ammonium salt are claimed, e.g. pyrrollidinium, piperidinium, morpholinium, adamantylammonium, N,N-dicyclohexylammonium, N-methyl-cyclohexylammonium, tert-octylammonium. The method for preparation of some representatives of the ammonium salts has been disclosed, including rosuvastatin TBA salt of the Formula (III). Nevertheless the salt has not been characterized by analytical data. According to the disclosed methods, rosuvastatin TBA salt of the Formula (III) has not been used as starting material for the preparation of rosuvastatin calcium salt of the Formula (IV). The hydrolysis of the rosuvastatin esters is carried out in an autoclave in aqueous solution at a temperature around 100° C. However, the quality of the ammonium salts thus obtained is inferior to those obtained by other methods known from the state of the art. Depending on the quality of the amine used in the reaction, the purity of the product lies between 94.5 and 98.9% as determined by HPLC. In the case when tert-butylamine is used, the purity of the product is 98.4%. This purity can not be improved later since during the transformation of rosuvastatin TBA salt into rosuvastatin calcium salt of the Formula (IV), further purification can not be achieved and the state of the art is silent about a method for purification of rosuvastatin calcium salt of the Formula (IV) or rosuvastatin zinc salt of the Formula (V).

In Published International Patent Applications WO 2007125547 and WO 2008044243, methods have been disclosed for the preparation of rosuvastatin TBA salt of the Formula (III) starting from rosuvastatin sodium salt and for preparation of rosuvastatin calcium salt of the Formula (IV) starting from rosuvastatin TBA salt using the sodium salt as an intermediate. The method is carried out in an aqueous solution followed by the isolation of the calcium salt by filtration. The purity of the product has not been disclosed. In International Patent Application WO 2007125547, a crystalline modification of rosuvastatin TBA salt has been disclosed and characterized by powder X-ray diffractogram. In the same application, rosuvastatin butyl-, isobutyl- and sec-butylammonium salts are also claimed.

In Published International Patent Application WO 2010082072, methods have been disclosed for the transformation of rosuvastatin TBA salt of the Formula (III) into rosuvastatin calcium (2:1) salt of the Formula (IV) and into rosuvastatin zinc (2:1) salt of the Formula (V) using ethylacetate-water biphasic solvent system.

The objective of our research-development work was to provide a method suitable for the industrial manufacturing of rosuvastatin TBA salt of the Formula (III) in high purity complying with the internationally accepted guidelines by transforming a rosuvastatin ester of the general Formula (II) wherein R represents methyl, ethyl or tert-butyl, using mild reaction conditions in water or in a mixture of water and a water-miscible organic solvent.

Our objective has been solved according to the present invention.

It is well known from the state of the art that most of the methods starting from a rosuvastatin ester proceeds through the rosuvastatin sodium salt intermediate and rosuvastatin calcium directly obtained by this method is of unsatisfactory quality. Thus the sodium salt is often transformed into an ammonium salt suitable for recrystallization. Thus, the necessary purification may be achieved by the recrystallization of the ammonium salt intermediate. Subsequently the ammonium salt is converted back to rosuvastatin sodium salt using sodium hydroxide, which upon reacting with a calcium cation source, yields rosuvastatin calcium salt. Such processes include several unnecessary steps, which—even by the most careful implementation—most probably result in the increase of the concentration of the impurities due to the easily decomposing character and light sensitivity of rosuvastatin. Thus, usually neither the final product, nor the ammonium salt prepared in this way satisfies the regulations set forth by the ICH Guideline relating to impurities.

SUMMARY OF THE INVENTION

The present invention is specifically related to an industrially applicable method for the preparation of rosuvastatin tert-butylammonium (TBA) salt of the Formula (III) in high purity. According to the method, a starting material selected from rosuvastatin methylester of the Formula (IIa), rosuvastatin ethylester of the Formula (IIb) or rosuvastatin tert-butylester of the Formula (IIc) is directly reacted in a suitable solvent with tert-butylamine and the thus formed rosuvastatin TBA salt of the Formula (III) is isolated. It has been found that the most advantageously, a crystalline ester of the general Formula (II), wherein R represents methyl, ethyl or tert-butyl, can be used as starting material.

According to a further aspect of the present invention, there are provided methods for the preparation of new crystalline forms of rosuvastatin methylester of the Formula (IIa) and rosuvastatin ethylester of the Formula (IIb).

According to a still further method of the present invention, there are provided methods for the preparation of crystalline Form II and amorphous rosuvastatin TBA salt, which are suitable as reference material in the analytical testing related to the morphology of rosuvastatin TBA salt of the Formula (III).

In the method according to the present invention, a rosuvastatin ester of the general Formula (II), wherein the meaning of R is methyl, ethyl or tert-butyl, preferably a crystalline form thereof, the most preferably crystalline Form II rosuvastatin methylester of the Formula (IIa) or crystalline Form II rosuvastatin ethylester of the Formula (IIb) are reacted in water, in a polar solvent or in a mixture thereof with aqueous tert-butylamine solution, water is removed from the product and the thus obtained rosuvastatin TBA salt of the Formula (III) is isolated.

Under the reaction conditions applied, it was expected that the starting material or the product is at least partially converted into rosuvastatin tert-butylamide of the Formula (VII)

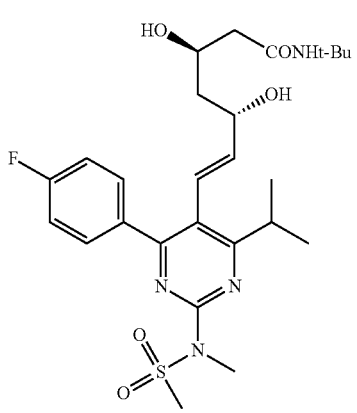

(VII)

which has to be removed in a separate purification step. As it is known from the state of the art, esters (in presence of an amine) or ammonium salts of carboxylic acids can easily transform into the corresponding amide upon heating. Such a side reaction, if present, would decrease the yield of the main reaction and would have result in a crystallizing impurity having high melting point which is difficult to remove from the rosuvastatin TBA product. Surprisingly, it has been found that no such byproduct has been formed in a detectable quantity, the yield of the reaction exceeded 90% and the purity of the TBA salt in several cases exceeded 99.9%. Manufacturing of a product is such high purity without applying any purification steps in itself is very surprising.

DETAILED DESCRIPTION OF THE INVENTION

According to one aspect, the present invention is related to a method form the preparation of rosuvastatin TBA salt of the Formula (III), which comprises reacting a rosuvastatin ester of the Formula (II), wherein R represents methyl, ethyl or tert-butyl in a polar solvent, preferably in water or in a mixture of water and a polar solvent such as water, methanol, acetonitrile, the most preferably in acetonitrile with 1.5 to 5 molar equivalents, preferably 2.0 molar equivalents of tert-butylamine at a temperature between 10 C and the boiling point of the solvent, preferably at a temperature between 25 to 50 C for 24 to 72 hours, preferably for about 40 hours. Subsequently, after the removal of water, the product is filtered and washed, thus rosuvastatin TBA salt of the Formula (III) is obtained in good yield and high purity. In this way, by reacting a rosuvastatin ester with tert-butylamine directly, rosuvastatin TBA salt having 99.8-99.9% purity (as determined by HPLC) can be produced, which is devoid of any impurity exceeding the limit concentration of 0.1% set forth by international guidelines and compendia. The product is of outstanding purity which does not necessitates further recrystallization. Rosuvastatin TBA salt obtained according to the method of the present invention is directly suitable for the preparation of rosuvastatin calcium (2:1) salt or rosuvastatin zinc (2:1) salt in anhydrous or hydrated form, having 99.8-99.9% purity (as determined by HPLC).

A further advantage of the method according to the present invention resides in that it can be carried out in a single reactor and extraction or chromatography steps requiring large amounts of organic solvent as well as manpower are not necessary.

By carrying out the method according to the present invention, we have found that in most cases, a rosuvastatin TBA product of the Formula (III) having uniform morphology can be obtained. However, in the case when the solution of the final product of the Formula (III) is subjected to fractionated crystallization, a new, essentially homogeneous crystalline form of rosuvastatin TBA salt could be obtained.

According to a further aspect of the present invention, there is provided crystalline Form II rosuvastatin TBA salt of the Formula (III).

Characteristic powder X-ray reflections of the new crystalline Form II rosuvastatin TBA salt of the Formula (III) are summarized in Table 1. The X-ray diffractogram of the same substance is shown in FIG. 1.

TABLE 1

Positions of the X-ray reflections of crystalline Form II rosuvastatin TBA salt [compound of the Formula (III)] (2 ± 0.2) and relative intensities (>10%)

| Peak No. | Angle 2-Theta (degrees) | d value Angstrom | Intensity % |
|---|---|---|---|
| 1 | 5.481 | 16.11132 | 8.1 |
| 2 | 5.957 | 14.82335 | 7.1 |
| 3 | 10.529 | 8.39561 | 27.0 |
| 4 | 11.282 | 7.83634 | 31.4 |
| 5 | 15.457 | 5.72793 | 16.8 |
| 6 | 15.803 | 5.60353 | 69.9 |
| 7 | 16.231 | 5.45656 | 13.7 |
| 8 | 16.682 | 5.31014 | 10.9 |
| 9 | 18.651 | 4.75363 | 100 |
| 10 | 19.05 | 4.65489 | 28.5 |
| 11 | 19.832 | 4.47316 | 31.4 |
| 12 | 20.512 | 4.32646 | 28.1 |
| 13 | 21.098 | 4.20759 | 12.5 |
| 14 | 22.492 | 3.94978 | 24.1 |
| 15 | 27.205 | 3.27526 | 14.6 |
| 16 | 30.409 | 2.93708 | 9.7 |

Measurement conditions and apparatus for powder X-ray diffractometry

Apparatus: BRUKER D8 ADVANCE powder iffractometer
Radiation: CuK$_1$(1.54060 Å), CuK$_2$(1.54439 Å)
Voltage: 40 kV
Anode current: 30 mA
Accessories: Göbel-mirror
 Soller-slit
 sample changer, transmission position
Detector: LynxEye
Measurement: continous/scan: 4-352
Step: 0.02
Sample: without pulverization, measured at room temperature It is well known in the state of the art that crystalline forms of the same chemical compound can have significantly different physical-chemical characteristics, e.g. stability, filterability, drying speed, dissolution rate etc. In an industrial manufacturing process, it is of paramount importance that the properties of the manufactured batches influencing further manufacturing operations should be reproducible. Such characteristics are closely related to the morphology of the drug substance or that of an intermediate thereto. Thus analytical testing of the morphology of the product is an important analytical task. Crystalline Form II rosuvastatin TBA salt can be used as an analytical reference material during the testing of rosuvastatin TBA salt of the Formula (III).

Similarly, in order to support analytical testing, the amorphous form of rosuvastatin TBA salt of the Formula (III) has been prepared.

According to a further aspect of the present invention, there is provided amorphous rosuvastatin TBA salt of the Formula (III). Amorphous rosuvastatin TBA salt can be prepared by dissolving rosuvastatin TBA salt in a saturated aliphatic alcohol having one to four carbon atoms, preferably in methanol, the solvent is removed and the solid residue is dried at room temperature for at least one day.

Powder X-ray diffractogram of amorphous rosuvastatin TBA salt of the Formula (III) is shown in FIG. 2. Measuring conditions are the same as described above in connection with crystalline Form II rosuvastatin TBA salt.

Rosuvastatin TBA salts of different morphology, such as crystalline Form I rosuvastatin TBA salt known from the state of the art, the new crystalline Form II rosuvastatin TBA salt according to the present invention and new amorphous rosuvastatin TBA salt as disclosed above, can be used as reference materials during the analytical testing and crystallographic studies related to rosuvastatin TBA salts of the Formula (III).

According to the state of the art, it is known that pretreatment of samples prior to powder X-ray diffractometric analysis, such as pulverization can significant influence powder X-ray measurement results. Therefore no pretreatment has been applied before the testing.

The person skilled in the art identifies the solid state morphology of a known chemical compound by its powder X-ray diffractogram and specific signals (reflexions) thereof (diffraction angle, relative intensity) by comparing the diffractogram to that of a reference material or to specific signals obtained from the measurement of such material. Such identification is especially important in case of compound having multiple solid state (amorphous and crystalline) forms.

Crystalline Form II rosuvastatin TBA salt of the Formula (III) exhibits the X-ray diffraction signal of greatest intensity at 18.651° 2.

X-ray diffraction signals of crystalline Form II rosuvastatin TBA salt exceeding 50% relative intensity are the following: 15.803 and 18.651° (2).

X-ray diffraction signals of crystalline Form II rosuvastatin salt of the Formula (III) exceeding 25% relative intensity are the following: 11.282, 15.803, 18.651, 19.050, 19.832 és 20.512° (2).

According to a further aspect of the present invention, there is provided a method for the preparation of crystalline Form II rosuvastatin TBA salt of the Formula (III), which comprises suspending a rosuvastatin ester of the general Formula (II), wherein R represents methyl, ethyl or tert-butyl, preferably in crystalline form in water, an aqueous solution containing an equimolar amount of tert-butylamine is added thereto at a temperature between 10 and 50 C, preferably at 25 C, optionally the addition of tert-butylamine is repeated within a period of 2 to 24 hours in one to five times in a way that at each subsequent addition, an aqueous solution containing 0.1 to 0.5, preferably 0.2 molar equivalents of tert-butylamine are added, the precipitated solids are removed after 72 to 96 hours and the thus obtained crystalline Form II rosuvastatin TBA salt of the Formula (III) is isolated after further 48-72 hours of crystallization.

According to a more advantageous embodiment of the present invention a crystalline rosuvastatin ester of the Formula (II), wherein the meaning of R is as defined above, is used for the preparation of rosuvastatin TBA salt. The most preferably, a high purity crystalline ester of the Formula (II) is used. It has been found that the purity of the starting material is significantly influenced by its solid state and morphology. Furthermore, we have also established that the quality of the starting material has great effect on the purity of the final product.

According to this embodiment, the new crystalline Form II rosuvastatin methylester of the Formula (IIa) or the new crystalline Form II rosuvastatin ethylester of the Formula (IIb) are especially advantageous starting materials.

Esters of the Formula (II), wherein the meaning R is as defined above, are available commercially as impure (90-95% chemical purity), sometimes coloured, viscous oily liquids or in somewhat greater purity, as solids. For example, in European Patent No. 521471, rosuvastatin methylester of the Formula (IIa) is characterized as a viscous oil, which is purified before further use by column chromatography. According to a method disclosed in Published International Patent Application WO 2009019211, rosuvastatin methylester of the Formula (IIa) is prepared by subjecting crude rosuvastatin methylester to preparative high-performance liquid chromatography. According to the method disclosed in Published International Patent Application WO 2005042522, crystalline rosuvastatin ethylester of the Formula (IIb) is obtained by adsorptive purification on silica gel using hexane-toluene solvent mixture.

During our experiments directed to the further purification of commercial rosuvastatin methylester and ethylester, we have surprisingly found that a new crystalline form of each ester can be prepared. By crystallizing rosuvastatin methylester from different solvents and solvent mixtures, we obtained the new crystalline form which indicates the higher stability of said new form.

The fact that rosuvastatin esters of the Formulae (IIa) and (IIb) can be prepared in crystalline form without using a chromatographic or adsorptive methods is very surprising in itself. Crystalline forms of the compounds of the Formulae (IIa) and (IIb) are especially suitable starting materials for the preparation of rosuvastatin TBA salt.

According to a further aspect of the present invention there is provided new crystalline Form II rosuvastatin methylester of the Formula (IIa). Powder X-ray diffractogram of the new form II rosuvastatin methylester is depicted in FIG. 3. Powder X-ray diffraction data of the new crystalline methylester are summarized in Table 2. The measuring conditions for powder X-ray diffractometry are identical to those described in relation to crystalline Form II rosuvastatin TBA salt.

TABLE 2

Powder X-ray diffraction data of crystalline Form II rosuvastatin methylester [compound of the Formula (IIa)] (2 ± 0.2) and relative intensities (>5%)

| Peak No. | Angle 2-Theta ° | d value Angstrom | Intensity % |
|---|---|---|---|
| 1 | 8.721 | 10.13081 | 16.7 |
| 2 | 9.371 | 9.43010 | 63.6 |
| 3 | 9.681 | 9.12830 | 21.4 |
| 4 | 12.071 | 7.32604 | 8.9 |
| 5 | 13.776 | 6.42304 | 6.9 |
| 6 | 15.261 | 5.80119 | 5.6 |
| 7 | 15.551 | 5.69369 | 5.6 |
| 8 | 15.933 | 5.55810 | 23 |
| 9 | 16.519 | 5.36211 | 12.2 |
| 10 | 16.660 | 5.31699 | 9.5 |
| 11 | 17.471 | 5.07202 | 75.3 |
| 12 | 18.042 | 4.91268 | 100 |
| 13 | 18.836 | 4.70745 | 14.5 |
| 14 | 19.553 | 4.53629 | 87.7 |
| 15 | 19.827 | 4.47435 | 20.9 |
| 16 | 20.239 | 4.38416 | 22.8 |
| 17 | 20.675 | 4.29262 | 11.9 |
| 18 | 21.254 | 4.17702 | 10.7 |
| 19 | 21.695 | 4.09302 | 53.7 |
| 20 | 22.374 | 3.97039 | 13.3 |
| 21 | 22.707 | 3.91291 | 5.2 |
| 22 | 23.143 | 3.84011 | 11.6 |
| 23 | 23.538 | 3.77661 | 7.1 |

TABLE 2-continued

Powder X-ray diffraction data of crystalline Form II rosuvastatin methylester [compound of the Formula (IIa)] (2 ± 0.2) and relative intensities (>5%)

| Peak No. | Angle 2-Theta ° | d value Angstrom | Intensity % |
|---|---|---|---|
| 24 | 23.815 | 3.73326 | 10 |
| 25 | 24.365 | 3.65023 | 32.3 |
| 26 | 24.773 | 3.59108 | 24.6 |
| 27 | 25.091 | 3.54626 | 7.7 |
| 28 | 26.352 | 3.37933 | 29.2 |
| 29 | 27.369 | 3.25605 | 6.7 |
| 30 | 29.569 | 3.01864 | 6.6 |
| 31 | 29.812 | 2.99458 | 7.6 |
| 32 | 30.892 | 2.89228 | 5 |
| 33 | 31.260 | 2.85903 | 5 |
| 34 | 32.475 | 2.75484 | 8 |
| 35 | 33.678 | 2.65910 | 7.6 |

Powder X-ray diffraction signals having the highest relative intensity in the diffractogram of crystalline Form II rosuvastatin methylester of the Formula (IIa) can be observed at 17.471, 18.042 and 19.553° 2.

Powder X-ray diffraction signals of crystalline Form II rosuvastatin methylester of the Formula (IIa) having at least 50% relative intensity are the following: 9.371, 17.471, 18.042, 19.553, and 21.695° (2).

Powder X-ray diffraction signals of crystalline Form II rosuvastatin methylester of the Formula (IIa) having at least 25% relative intensity are the following 9.371, 17.471, 18.042, 19.553, 21.695, 24.365 and 26.352° (2).

According to a further aspect of the present invention, there is provided method for the preparation of crystalline Form II rosuvastatin methylester of the Formula (IIa), wherein crystalline Form I or non-crystalline or oily liquid rosuvastatin methylester of the Formula (IIa) is
  a) dissolved in a polar solvent, preferably in a saturated aliphatic alcohol having one to four carbon atoms, or in N,N-dimethylformamide, the most preferably in ethanol optionally by heating, the solution is mixed with water and after cooling and optionally stirring the mixture for 24 to 168 hours at room temperature, crystalline Form II rosuvastatin methylester of the Formula (IIa) is isolated; or
  b) crystallized from a mixture of water and a polar solvent, preferably a mixture of water and a saturated aliphatic alcohol having one to four carbon atoms or water and N,N-dimethylformamide and after optionally stirring the solution for 24 to 72 hours at room temperature, crystalline Form II rosuvastatin methylester of the Formula (IIa) is isolated.

According to a still further aspect of the present invention, there is provided crystalline Form II rosuvastatin ethylester of the Formula (IIb), which is characterized by the powder X-ray diffractogram of FIG. 4 and diffraction data of Table 3.

Measurement conditions for powder X-ray diffractometry measurement are identical to those described for crystalline Form II rosuvastatin methylester.

Powder X-ray diffraction signal having the greatest intensity being suitable for the identification of crystalline Form II rosuvastatin ethylester of the Formula (IIb) can be found at 17.907 and 19.419 degrees 2⁻

Powder X-ray diffraction signals of crystalline Form II rosuvastatin ethylester of the Formula (IIb) having relative intensity exceeding 50% can be found at 9.238, 17.313, 17.907 and 19.419 degrees (2).

Powder X-ray diffraction signals of crystalline Form II rosuvastatin ethylester of the Formula (IIb) exceeding 25% relative intensity can be found at 9.238, 9.638, 16.354, 17.313, 17.907, 19.419, 20.137, 21.478, 24.112, 24.376, 24.684 and 26.030 degrees (2).

TABLE 3

Powder X-ray diffractometric data of crystalline Form II rosuvastatin ethylester [compound of the Formula (IIb)] diffraction angles (2 ± 0.2) and relative intensities (>5%)

| Peak No. | Angle 2-Theta ° | d value Angstrom | Intensity % |
|---|---|---|---|
| 1 | 8.717 | 10.13632 | 12.6 |
| 2 | 9.238 | 9.56503 | 65.2 |
| 3 | 9.638 | 9.16899 | 39.7 |
| 4 | 11.942 | 7.40520 | 6.5 |
| 5 | 13.737 | 6.44123 | 5.7 |
| 6 | 15.056 | 5.87970 | 4.6 |
| 7 | 15.457 | 5.72793 | 5.7 |
| 8 | 15.846 | 5.58843 | 17.5 |
| 9 | 16.354 | 5.41578 | 25.2 |
| 10 | 17.313 | 5.11788 | 68.3 |
| 11 | 17.907 | 4.94952 | 100 |
| 12 | 18.553 | 4.77863 | 16.8 |
| 13 | 19.419 | 4.56742 | 89 |
| 14 | 20.137 | 4.40611 | 27.1 |
| 15 | 20.574 | 4.31357 | 13.1 |
| 16 | 21.005 | 4.22599 | 6.1 |
| 17 | 21.478 | 4.13388 | 47.3 |
| 18 | 21.775 | 4.07824 | 7.4 |
| 19 | 22.304 | 3.98270 | 19.1 |
| 20 | 22.845 | 3.88962 | 12.8 |
| 21 | 23.448 | 3.79084 | 14.5 |
| 22 | 23.630 | 3.76213 | 17.4 |
| 23 | 24.112 | 3.68803 | 34.7 |
| 24 | 24.376 | 3.64866 | 29.3 |
| 25 | 24.684 | 3.60385 | 25.5 |
| 26 | 26.030 | 3.42042 | 37.7 |
| 27 | 27.068 | 3.29152 | 5.6 |
| 28 | 29.128 | 3.06330 | 10.9 |
| 29 | 29.416 | 3.03392 | 7.7 |
| 30 | 30.412 | 2.93678 | 5 |
| 31 | 30.984 | 2.88386 | 5.9 |
| 32 | 31.271 | 2.85806 | 5.5 |
| 33 | 32.027 | 2.79234 | 5.1 |
| 34 | 33.062 | 2.70725 | 11 |
| 35 | 33.981 | 2.63611 | 5 |

During the recrystallization experiments related to rosuvastatin ethylester of the Formula (IIb) from different solvents, we have found that in most cases the new crystalline Form II rosuvastatin ethylester was formed, which indicates higher stability thereof. In the experiment wherein the rosuvastatin ethylester polymorph prepared according to the method of WO 2005042522 (designated in this specification as Form I) together with the new crystalline Form II rosuvastatin ethylester according to the present invention were suspended in solvent for a longer period of time, rosuvastatin ethylester has been transformed fully into crystalline Form II, which proves the higher thermodynamic stability of the new polymorph.

According to a further aspect of the present invention, there is provided a method for the preparation of crystalline Form II rosuvastatin ethylester of the Formula (IIb), wherein solid crystalline Form I or solid non-crystalline or liquid rosuvastatin ethylester of the Formula (IIb) is
  a) dissolved in a polar solvent, preferably selected from saturated aliphatic alcohols comprising one to four carbon atoms, acetonitrile or N,N-dimethyl-formamide, preferably in ethanol optionally by heating, the solution is mixed with water and after cooling and optionally stirring for 24 to 168 hours at room temperature, crystalline Form II rosuvastatin ethylester is isolated; or b) crystallized from a mixture of water and a polar solvent, preferably a mixture of water with a saturated aliphatic alcohol having one to four carbon atoms, acetonitrile or N,N-dimethyl-formamide, the reaction mixture is optionally stirred for 24 to 72 hours and crystalline Form II rosuvastatin ethylester of the Formula (IIb) is isolated; or c) crystallized from a solvent selected from saturated aliphatic esters comprising four to eight carbon atoms, saturated aliphatic or cyclic ethers comprising four to eight carbon atoms, saturated aliphatic ketones comprising three to six carbon atoms, an aromatic hydrocarbon type solvent or from a mixture of any of the above-mentioned solvents and water, the reaction mixture is optionally stirred at room temperature for 24 to 72 hours and crystalline Form II rosuvastatin ethylester is isolated; or d) dissolved in a solvent selected from saturated aliphatic esters having four to eight carbon atoms, saturated aliphatic or cyclic ethers comprising four to eight carbon atoms or aliphatic ketones comprising three to six carbon atoms ad aromatic hydrocarbons and after adding a saturated aliphatic or alicyclic hydrocarbon, preferably hexane, heptane or cyclohexane, crystallin Form II rosuvastatin ethylester is crystallized and the crystals are optionally stirred for 24 to 72 hours and isolated.

We have found that by using rosuvastatin methylester of the Formula (IIa) or rosuvastatin ethylester of the Formula (IIb), especially using the new crystalline forms thereof in the method according to the present invention, rosuvastatin TBA salt of the Formula (II) can be obtained in an unexpectedly high purity of approx. 99.9%.

Thus during our research-development work by using new crystalline forms of rosuvastatin esters of the general Formula (II) exhibiting higher stability than those known from the state of the art, a one-step method has been provided for the preparation of high purity rosuvastatin TBA salt, which is simple, provides good yield and amenable to industrial application. Rosuvastatin TBA salt of the Formula (III) thus obtained can be transformed according to methods known from the prior art into rosuvastatin calcium (2:1) or rosuvastatin zinc (2:1) salt.

Further aspects of the present invention are demonstrated by the following examples without restricting the invention to the examples.

Preparation of Rosuvastatin Ethylester Polymorph Disclosed in Published International Patent Application WO 2005042522 [Crystalline Form I Rosuvastatin Ethylester of the Formula (IIb)]

Reference Example 1

0.50 g (0.98 mmol) of rosuvastatin ethylester are dissolved in 10 cm$^3$ hot water and allowed to cool to 25° C. The product is first separates in form of the oil and during the 24-hour stirring period, gradually crystallizes. The product is filtered and washed with water. Thus 0.31 g (62%) of title compound are obtained.

Reference Example 2

0.50 g (0.98 mmol) of rosuvastatin ethylester are dissolved in 1 cm$^3$ hot ethylacetate and 4.5 cm$^3$ of n-hexane are added with stirring. The mixture is cooled to 25° C., while the product gradually precipitated. The solids are filtered, washed with n-hexane and dried. Thus 0.49 g (98%) of title compound are obtained.

Preparation of Starting Materials

Transformation of Rosuvastatin Ethylester Polymorph Prepared According to Published International Patent Application WO 2005042522 [Crystalline Form I Rosuvastatin Ethylester of the Formula (IIb)] into Crystalline Form II Rosuvastatin Ethylester Crystalline Form I rosuvastatin ethylester of the Formula (IIb) is obtained according to the method disclosed in Published International Patent Application WO 2005042522.

In the recrystallization experiments described below, the filtered product is dried at 30° C. in 100-150 mbar vacuum. In all experiments crystalline Form II rosuvastatin ethylester of the Formula (IIb) exhibiting the powder X-ray diffractogram and reflections essentially as demonstrated in FIG. 4 and Table 3.

Example 1

0.50 g (0.98 mmol) of crystalline Form I rosuvastatin ethylester (prepared according to WO 2005042522) were dissolved in 1 cm$^3$ of hot ethanol and 3 cm$^3$ of water are added dropwise. The product initially separates as an oil, which by the next day gradually turns into a mixture of crystalline and oily phase. Thereafter 5 cm$^3$ of water are added and the mixture is stirred for 30 hours at 25° C. Thus 0.47 g (94%) of crystalline Form II rosuvastatin ethylester exhibiting the reflexions disclosed in Table 3 and showing the diffractogram of FIG. 4 are obtained.

Example 2

0.50 g (0.98 mmol) of rosuvastatin ethylester are dissolved in 1.5 cm$^3$ of hot 1:1 (v/v) ethanol-water solvent mixture. The solution is allowed to cool to 25° C. with stirring. After 10 minutes a thick suspension is formed. The product is filtered and dried. Thus 0.38 g (76%) of product are obtained.

Example 3

0.50 g (0.98 mmol) of rosuvastatin ethylester are dissolved in 1 cm$^3$ 4:1 (v/v) hot ethanol-water mixture and cooled to 25° C. with stirring. Thus a thick suspension is obtained. The solids are filtered and dried. Thus 0.24 g (48%) of product are obtained.

Example 4

0.50 g (0.98 mmol) of rosuvastatin ethylester are dissolved in 1 cm$^3$ of hot ethanol. By cooling the mixture to 25° C., a solidified mass is obtained, which is diluted with 0.5 cm$^3$ of ethanol cooled to 0-5° C. The solids are filtered and dried. Thus 0.30 g (60%) of product are obtained.

Example 5

0.50 g (0.98 mmol) of rosuvastatin ethylester are dissolved in 5 cm$^3$ ethanol at 25° C. and 12 cm$^3$ of water having the temperature of 25° C. are added gradually in small portions. The mixture becomes opalescent and the separated product crystallizes upon stirring. The solids are filtered and dried. Thus 0.48 g (96%) of product are obtained.

Example 6

0.50 g (0.98 mmol) of rosuvastatin ethylester are dissolved in 1.5 cm³ of hot 1:1 (v/v) methanol-water mixture. After cooling to 25° C., the oily mixture gradually crystallizes and turns to a suspension. The solids are filtered and dried. Thus 0.46 g (92%) of product are obtained.

Example 7

0.50 g (0.98 mmol) of rosuvastatin ethylester are dissolved in 0.6 cm³ hot methanol. The mixture is cooled to 25° C. in the first step, thereafter to 0-5° C. The product separates gradually. The solids are filtered and dried. Thus 0.34 g (68%) of product are obtained.

Example 8

1.0 g (1.96 mmol) of rosuvastatin ethylester are dissolved in 2 cm³ of 5:1 (v/v) methanol-water mixture at 60° C. and cooled with tap water. In 10 minutes, the crystallization is started. Thereafter further 11 cm³ of the same solvent mixture cooled to 0-5° C. were added in order to obtain a mixture amenable to stirring. The mixture is stirred for further 16 hours, filtered and dried. Thus 0.79 g (79%) of product are obtained.

Example 9

1.0 g (1.96 mmol) of rosuvastatin ethylester are dissolved in 2 cm³ 5:1.5 (v/v) methanol-water mixture at 60° C. By cooling with tap water while stirring continuously, the crystallization is started. After about half an hour, the mixture became thick. At this stage, the mixture is diluted with 9 cm³ of the same solvent mixture and stirred for 20 hours at 25° C. and for five hours at 0-5° C. The solids are filtered off and dried. Thus 0.91 g (91%) of product are obtained.

Example 10

0.50 g (0.98 mmol) of rosuvastatin ethylester are dissolved in 0.6 cm³ of hot methanol. Gradually in small portions, 1 cm³ of water are added. After initial opalescence, the product separates turbidly. The mixture is cooled to 25° C. and after two hours, the crystalline mass is filtered and dried. Thus 0.47 g (94%) of product are obtained.

Example 11

0.50 g (0.98 mmol) of rosuvastatin ethylester are dissolved in 1.5 cm³ methanol at 25° C. and gradually 3.5 cm³ of distilled water having the temperature of 25° C.—are added in portions. The initially oily product is turned into crystalline in half an hour. The product is filtered and dried. Thus 0.46 g (92%) of product are obtained.

Example 12

0.50 g (0.98 mmol) of rosuvastatin ethylester are dissolved in 0.6 cm³ of hot methanol. The solution is gradually cooled to 25° C. and during this time, 1.5 cm³ of cyclohexane are added dropwise. The product initially separates in oily form, thereafter crystallizes upon trituration and cooling. In 48 hours, a product suitable for filtering is obtained. The solids are filtered and dried. Thus 0.42 g (84%) of product are obtained.

Example 13

0.50 g (0.98 mmol) of rosuvastatin ethylester are dissolved in 0.6 cm³ hot methanol. The solution is cooled to 25° C. gradually, while 1.5 cm³ of n-hexane are added dropwise. The product separates initially as an oil, which gradually crystallizes upon trituration and cooling. After 48 hours, a product suitable for filtering is obtained. The solids are filtered and dried. Thus 0.44 g (88%) of product are obtained.

Example 14

0.50 g (0.98 mmol) of rosuvastatin ethylester are dissolved in 0.6 cm³ of hot methanol. The solution is cooled to 25° C. gradually, while 1.5 cm³ of n-heptane are added dropwise. The product separates first as an oil which is crystallizing upon trituration and cooling. After 48 hours, a product suitable for filtering is obtained. The solids are filtered and dried. Thus 0.49 g (98%) of title product are obtained.

Example 15

0.50 g (0.98 mmol) of rosuvastatin ethylester are dissolved in 1 cm³ of hot isopropanol. The solution is cooled first to 25° C. thereafter to a temperature between 0-5° C. The product separates slowly, thereafter filtered and dried. Thus 0.34 g (68%) of product are obtained.

Example 16

050 g (0.98 mmol) of rosuvastatin ethylester are dissolved in 1.5 cm³ of hot 1:1 (v/v) isopropanol-water mixture. Upon cooling to 25° C., the oily mixture crystallizes gradually and during further cooling, it turns into a thick suspension. The suspension is diluted with 1 cm³ of the same solvent mixture cooled to 5° C. The product is filtered and dried. Thus 0.39 g (78%) of product are obtained.

Example 17

0.50 g (0.98 mmol) of rosuvastatin ethylester are dissolved in 1 cm³ of hot isopropanol. 1 cm³ of water are added thereto. The product starts to separates in an oily form, which crystallizes by the next day. The solids are filtered and dried. Thus 0.45 g (90%) of product are obtained.

Example 18

0.50 g (0.98 mmol) of rosuvastatin ethylester are dissolved in 0.25 cm³ of hot n-butanol. Upon cooling, the product starts to separate in oily form, which later crystallizes and at the temperature of 25° C., it turns into a thick suspension. The suspension is diluted with 0.25 cm³ of n-butanol cooled to 5° C. The solids are filtered and dried. Thus 0.16 g (32%) of product are obtained.

Example 19

0.50 g (0.98 mmol) of rosuvastatin ethylester are dissolved in 0.25 cm³ of hot n-butanol and 1 cm³ of water are added thereto. The product separates in oily form in the beginning, which crystallized by the next day. The thick suspension is diluted with 5 cm³ of water. The solids are filtered and dried. Thus 0.48 g (96%) of product are obtained.

Example 20

0.50 g (0.98 mmol) of rosuvastatin ethylester are dissolved in 0.7 cm³ of hot acetonitrile. Upon cooling to 25° C., the product separates slowly. The mixture is cooled further to a temperature between 0 and 5° C. By the next day, a thick crystalline mass is obtained. The mixture is diluted with acetonitrile cooled to a temperature between 0 and 5° C. to obtain a suspension suitable for filtration. The solids are filtered and dried. Thus 0.30 g (60%) of product are obtained.

Example 21

0.50 g (0.98 mmol) of rosuvastatin ethylester are dissolved in 2.5 cm³ acetonitrile at 25° C. Gradually 5 cm³ of water are added dropwise. The product separates initially in oily form, which crystallizes after 2 days. The thick mixture is diluted with 2.5 cm³ of water. The solids are filtered and dried. Thus 0.44 g (88%) of product are obtained.

Example 22

0.50 g (0.98 mmol) of rosuvastatin ethylester are dissolved in 0.7 cm³ of hot acetonitrile. While the solution is still warm, gradually 1.5 cm³ of water are added dropwise. The product, which separates initially as an oily, crystallizes by the next day. The product is filtered and dried. Thus 0.45 g (90%) of product are obtained.

Example 23

0.50 g (0.98 mmol) rosuvastatin ethylester are dissolved in 1 cm³ of hot ethylacetate. The mixture is cooled to 25° C., while the product is slowly separated. By cooling to a temperature between 0 to 5° C., a thick crystalline mixture is obtained by the next day. The product is filtered and dried. Thus 0.49 g (98%) of product are obtained.

Example 24

0.50 g (0.98 mmol) of rosuvastatin ethylester are dissolved in 1 cm³ of hot ethylacetate and gradually 7 cm³ of n-hexane are added dropwise. The product initially separates in an oily form, thereafter by cooling to 25° C. first and to a temperature between 0 to 5° C. and by trituration, it turns crystalline. The solids are filtered and dried. Thus 0.50 g (100%) of product are obtained.

Example 25

0.5 g (0.98 mmol) of rosuvastatin ethylester are dissolved in 1 cm³ of hot isopropylacetate. The solution is cooled to 25° C. and in the second step to a temperature between 0-5° C. By the next day, a thick crystalline mass is obtained. The solids are filtered and dried. Thus 0.25 g (50%) of product are obtained.

Example 26

0.50 g (0.98 mmol) of rosuvastatin ethylester are dissolved in 3.5 cm³ of hot tert-butylmethylether (MTBE). Upon cooling and trituration, the product separates continuously. The thick suspension is diluted with 2 cm³ of MTBE cooled to a temperature between 0 and 5° C. The separated product is filtered and dried. Thus 0.38 g (76%) of product are obtained.

Example 27

0.50 g (0.98 mmol) of rosuvastatin ethylester are dissolved in 0.5 cm³ of hot tetrahydrofurance (THF). Upon cooling to 0.25° C., thereafter to a temperature between 0 and 5° C., the product separates off. By the next day, a thick crystalline mass is obtained, which is diluted with 0.25 cm³ THF cooled to a temperature between 0 and 5° C. The separated product is filtered and dried. Thus 0.25 g (50%) of product are obtained.

Example 28

0.50 g (0.98 mmol) of rosuvastatin ethylester are stirred in 1.5 cm³ of diethylether at 35° C. and subsequently 0.3 cm³ of methanol are added dropwise until dissolution. The stirring is maintained and the mixture is allowed to cool to 25° C. During this period, the product continuously separates from the mixture. Thereafter 3 cm³ of diethylether are added, the product is filtered and dried. Thus 0.26 g (52%) of product are obtained.

Example 29

0.50 g (0.98 mmol) of rosuvastatin ethylester are dissolved in 0.75 cm³ of hot 2-methoxyethanol. Thereafter 2 cm³ of water are added dropwise. The product separates initially in an oily form and crystallizes upon cooling. The solids are filtered and dried. Thus 0.46 g (92%) of product are obtained.

Example 30

0.50 g (0.98 mmol) of rosuvastatin ethylester are dissolved in 0.75 cm³ of hot 2-methoxyethanol. 1 cm³ of cyclohexane are added dropwise. The product initially separates in an oily form which crystallizes by the next day. The solids are filtered and dried. Thus 0.46 g (92%) of product are obtained.

Example 31

0.50 g (0.98 mmol) of rosuvastatin ethylester are dissolved in 1 cm³ of hot toluene. By cooling, the product separates in a gelly form which turns into a thick crystalline mass in half an hour. The suspension is diluted with 0.1 cm³ of toluene cooled to a temperature between 0 and 5° C., filtered and dried. Thus 0.40 g (80%) of product are obtained.

Example 32

0.50 g (0.98 mmol) of rosuvastatin ethylester are dissolved in 0.5 cm³ hoz acetone. Upon cooling, the product begins to separate slowly. The suspension is diluted with 0.5 cm³ of cold (0-5° C.) acetone. The solids are filtered and dried. Thus 0.20 g (40%) of product are obtained.

Example 33a 0.50 g (0.98 mmol) of rosuvastatin ethylester are dissolved in 0.5 cm³ of hot acetone. Thereafter 2 cm³ of water are added dropwise. The product initially separates in an oily form, which crystallizes upon cooling. The solids are filtered and dried. Thus 0.50 g (100%) of product are obtained.

Preparation of Crystalline Form II Rosuvastatin Methylészter [Compound of the Formula IIa)]

Rosuvastatin methylester of the Formula (IIa) used as starting material has been obtained according to the method disclosed in European Patent No. 521471 in form of an oil after purification by column chromatography. In the methods disclosed below, the filtered product has been dried at 30° C. in vacuo at the pressure of 100-150 mbar. In all cases, crystalline Form II rosuvastatin methylester of the Formula (Iia) were obtained, for which the powder X-ray diffractogram is shown in FIG. 3 and the positions and relative intensities of diffraction signals are given in Table 2.

Example 34

0.50 g (1.0 mmol) of rosuvastatin methylester are dissolved in 1.5 cm$^3$ of hot 1:1 (v/v) ethanol-water solvent mixture and the solution is allowed to cool to 25° C. with stirring. The product separates as an oil. Thereafter the mixture is cooled to a temperature between 0 and 5° C., stirred for 48 hours, while the oil turns into a crystalline mass. The solids are filtered, dried at 30° C. and in vacuo (at 100-150 mbar). Thus 0.33 g (66%) of crystalline Form II product are obtained, for which the powder X-ray diffractogram is shown in FIG. 3 and the positions and relative intensities of diffraction lines are given in Table 2.

Example 35

0.50 g (1.0 mmol) of rosuvastatin methylester are dissolved in 0.25 cm$^3$ of hot methanol and while stirring, 1.25 cm$^3$ of water are added. A white oily phase is separated, which is allowed to cool to 25° C. while stirring. After stirring for 72 hours, the material becomes crystalline. The mixture is filtered and dried under the conditions given in Example 34. Thus 0.22 g (44%) of product are obtained having identical morphology to that of the product obtained in Example 34.

Example 36

0.30 g (0.60 mmol) of rosuvastatin methylester are dissolved in 0.2 cm$^3$ of hot N,N-dimethylformamide (DMF) and 2 cm$^3$ of water are added in portions. The product separates as a stickly oily mass. The mixture is allowed to cool to 25° C. with stirring. After 48 hours of stirring, the crystalline product obtained is filtered and dried according to the method described in Example 34. Thus 0.29 g (97%) of product having identical morphology to that of the product of Example 34 are obtained.

Example 37

0.20 g (0.40 mmol) of rosuvastatin methylester are dissolved in 2 cm$^3$ of hot isopropanol and 8 cm$^3$ of water are added in portions. The product separates as a sticky-oily mass. The mixture is allowed to cool to 25° C. After one week of stirring, the product turns into crystalline state. The crystals are filtered and dried according to the method of Example 34. Thus 0.15 g (75%) of product having identical polymorphism to that of the product obtained in Example 34.

Example 38

0.30 g (0.60 mmol) of rosuvastatin methylester are dissolved in 1 cm$^3$ of methanol at 25° C. and 3 cm$^3$ of water are added dropwise while stirring. The product separates as a sticky mass, which is crystallized during the 24-hour period of stirring. The crystals are filtered and dried according to the method described in Example 34. In this way 0.24 g (80%) of product having identical morphology to the product of Example 34 are obtained.

Example 39

0.30 g (0.60 mmol) of rosuvastatin methylester are dissolved in 0.4 cm$^3$ of DMF at 25° C. After adding 4 cm$^3$ of water, the product separates as an oily phase. After stirring for 24 hours, a crystalline product is obtained. The crystals are filtered and dried according to the method of Example 34. Thus 0.28 g (93%) of product having identical morphology to that of the product of Example 34 are obtained.

Preparation of Rosuvastatin TBA Salt [Compound of the Formula (III)] Starting from Crystalline Form II Rosuvastatin Methylester [Compound of the Formula (IIa)]

Example 40

10.0 g (0.020 mol) of crystalline Form II rosuvastatin methylester are dissolved in 70 cm$^3$ of acetonitrile while stirring at 25° C. Into the clear solution thus obtained are added 19.8 cm$^3$ of 1.0 M aqueous tert-butylamine (TBA) solution and in two hours period each, further 3.96 cm$^3$ portions of 1.0 M aqueous TBA solutions are added four times. Next morning a further 3.96 cm$^3$ portion of 1.0 M aqueous TBA solution are added. The mixture is stirred for further 24 hours, the solvents evaporated, ethylacetate is added and the remaining water is removed by azeotropic distillation. The suspension thus obtained is cooled to 5° C., stirred for one hour, filtered, washed with cold ethylacetate and dried. Thus 10.12 g (90%) of white product having purity (as assayed by HPLC) of 99.94% are obtained.

Example 41

30.0 g (0.061 mol) of crystalline Form II rosuvastatin methylester are suspended in 150 cm$^3$ of water with stirring at 25° C. Into the suspension thus obtained, 61 cm$^3$ of 1.0 M aqueous TBA solution are added. Thereafter in two hours periods, each time 12.2 cm$^3$ of 1.0 M aqueous TBA solution added to the reaction mixture four times. After 16 hours reaction time, a further 12.2 cm$^3$ portion of 1.0 M aqueous TBA solution are added and the reaction mixture is stirred for a further 24 hours. The product is filtered, washed with cold ethylacetate and dried. Thus 28.5 g (84%) of white product having purity (HPLC) of 99.98% are obtained.

Preparation of Rosuvastatin TBA Salt [Compound of the Formula (III)] Starting from Crystalline Form II Rosuvastatin Ethylester [Compound of the Formula (IIb)]

Example 42

30.0 g (0.059 mol) of crystalline Form II rosuvastatin ethylester are dissolved in 210 cm$^3$ of acetonitrile with stirring at 25° C. Into the solution thus obtained, 59.4 cm$^3$ of 1.0 M aqueous TBA solution are added. Subsequently in two hours periods, further 12 cm$^3$ portions of 1.0 M aqueous TBA solution are added four times. Next morning a further 6 cm$^3$ portion of 1.0 M aqueous TBA solution are added to the reaction mixture. After further 24 hours reaction time, acetonitrile is evaporated and 200 cm$^3$ of ethylacetate are added to the crystalline mass. Water is removed from the suspension thus obtained by azeotropic distillation. The mixture thus obtained is cooled to a temperature between 0 and 5° C., filtered, the filtered crystals are washed with cold ethylacetate and dried. Thus 31.14 g (95%) of white title product having purity (HPLC) of 99.86% are obtained.

Example 43

2.0 g (0.004 mol) of crystalline Form II rosuvastatin ethylester are dissolved in 14 cm$^3$ of acetonitrile and 7.5 cm$^3$ of aqueous 1.0 M TBA solution are added. The mixture is stirred in an autoclave at 25° C. for 48 hours. Thereafter the reaction mixture is evaporated and the remaining water is removed by azeotropic distillation with ethylacetate. The suspension thus obtained is cooled to a temperature between 0 and 5° C., filtered, the filtered solids are washed with cold ethylacetate and dried. Thus 1.90 g (91%) of product having purity as determined by HPLC of 99.86% are obtained.

Example 44

1.0 g (0.002 mol) of crystalline Form II rosuvastatin ethylester are dissolved in 7 cm$^3$ of acetonitrile and 2.18 cm$^3$ of 1.0 M aqueous TBA solution are added. The mixture is stirred in an autoclave at 25° C. and 2.5 bar pressure using argon atmosphere. After five hours, 0.6 cm$^3$ of 1.0 M aqueous TBA solution is added and the mixture is reacted for further 24 hours. Subsequently 1 cm$^3$ of 1.0 M aqueous TBA solution is added and the reaction is continued for further 24 hours. The reaction mixture is evaporated and the remaining water is removed by azeotropic distillation using ethylacetate. The suspension thus obtained is cooled to a temperature between 0 and 5° C., filtered, the filtered solids are washed with cold ethylacetate and dried. Thus 1.90 g (91%) of product having 99.86% purity (by HPLC) are obtained.

Example 45

10.0 g (0.02 mol) of crystalline Form II rosuvastatin ethylester are dissolved in 70 cm$^3$ of acetonitrile at 25° C. and 35.6 cm$^3$ of 1.0 M aqueous TBA solution are added. The mixture is stirred for 24 hours. Thereafter 2 cm$^3$ of 1.0 M aqueous TBA solution are added and the mixture is stirred for further 24 hours. The mixture is thereafter worked up according to method variant 1. Thus 8.69 g (80%) of product having HPLC purity of 99.90% are obtained.

Example 46

To 2.0 g (0.004 mol) of crystalline Form II rosuvastatin ethylester, 4.35 cm$^3$ of 1.0 M aqueous TBA solution are added. A thick suspension is formed, which is stirred at 25° C. for 2 hours. After this period, 0.4 cm$^3$ and two hours later, 2.4 cm$^3$ of 1.0 M aqueous TBA solution are added and stirred for further 3 hours. Subsequently 0.8 cm$^3$ of 1.0 M aqueous TBA solution are added and stirred overnight. The mixture is filtered, the filtered solids are washed by suspending in water and dried. Thus 1.76 g (81%) of product having HPLC purity of 99.56% are obtained.

Example 47

To 2.0 g (0.004 mol) of crystalline Form II rosuvastatin ethylester, 7.95 cm$^3$ of 1.0 M aqueous TBA solution are added. The suspension is stirred at 25° C. for 48 hours. The mixture is filtered, the filtered solids are washed with 2 cm$^3$ of water and dried. Thus 1.94 g (90%) of product having HPLC purity of 98.95% are obtained.

Example 48

30.0 g (0.059 mol) of crystalline Form II rosuvastatin ethylester are suspended in 120 cm$^3$ of water and 59.4 cm$^3$ of 1.0 M aqueous TBA solution are added at 25° C. with stirring. Thereafter four times in two hour periods, further 12 cm$^3$ portions of 1.0 M aqueous TBA solutions are added into the reaction mixture. Next morning further 6 cm$^3$ of 1.0 M aqueous TBA solution are added. The mixture is stirred for 24 hours, filtered and dried. Thus 23.2 g (71%) of product having HPLC purity of 99.50% are obtained.

Example 49

10.0 g (0.02 mol) of crystalline Form II rosuvastatin ethylester are suspended in 100 cm$^3$ of water and by stirring, 19.8 cm$^3$ of 1.0 M aqueous TBA solution are added at 25° C. Thereafter four times in two-hour periods, further 3.96 cm$^3$ of 1.0 M aqueous TBA solution are added to the reaction mixture each time. Next day the addition of 3.96 cm$^3$ of 1.0 M aqueous TBA solution is repeated twice in a two-hour period. The mixture is stirred for further 24 hours, thereby a clear solution is obtained. The product precipitates from the solution after one week. The solids are filtered and dried. Thus 7.89 g (73%) of product are obtained (purity by HPLC: 99.51%).

Preparation of Rosuvastatin TBA Salt [Compound of the Formula (III)] from Rosuvastatin Tert-Butylester [Compound of the Formula (IIc)]

Example 50

2.0 g (0.004 mol) of rosuvastatin tert-butylester are suspended in 14 cm$^3$ of acetonitrile and 3.7 cm$^3$ of 1.0 M aqueous TBA solution are added while stirring at 25° C. Thereafter five times in two-hour periods, further 0.8 cm$^3$ portions of 1.0 M aqueous TBA solution are added and stirred overnight. Subsequently the mixture is heated to 60° C. and after stirring for four hours, the temperature is raised to 80° C. After 6 hours, eight times in two-hour periods, each time a further 0.8 cm$^3$ of 1.0 M aqueous TBA solution are added to the reaction mixture. The mixture is boiled for further 27 hours and worked up. The reaction mixture is evaporated and the remaining water is removed by azeotropic distillation using ethylacetate. The suspension thus obtained is cooled to a temperature between 0 and 5° C., filtered, the filtered solids are washed with ethylacetate and dried. Thus 1.90 g (92%) product are obtained (HPLC purity: 99.60%).

Example 51

2.0 g (0.004 mol) of rosuvastatin tert-butylester are suspended in 14 cm$^3$ of acetonitrile and 13.4 cm$^3$ of 1.0 M aqueous TBA solution are added while stirring at 25° C. Thereafter the reaction mixture is heated to 80° C., boiled for 36 hours, evaporated and the remaining water is removed by azeotropic distillation with ethylacetate. The suspension thus obtained is cooled to a temperature between 0 and 5° C., filtered, the filtered solids are washed with cold ethylacetate and dried. Thus 1.90 g (92%) product are obtained. The product is suspended in 19 cm$^3$ of acetonitrile, heated to 80° C. and 17 cm$^3$ of isopropanol are added dropwise until dissolution. The thus obtained slightly opalescent solution is filtered and cooled to 25° C. in the first step, thereafter to a temperature between 0 and 5° C. while stirring. After 2 hours the solids are filtered, washed with cold acetonitrile and dried. Thus 1.70 g (85%) of product are obtained (HPLC purity: 99.90%).

Preparation of Crystalline Form II Rosuvastatin TBA Salt [Compound of the Formula (III)]

Example 52

5.0 g (0.01 mol) of crystalline Form II rosuvastatin ethylester are suspended in 65 cm³ of water and into this suspension, 9.9 cm³ of 1.0 M aqueous TBA solution are added while stirring at 25° C. Thereafter four times in two-hour periods further 1.98 cm³ of 1.0 M aqueous TBA solution are added to the reaction mixture. Next day twice in two-hour periods, further 2×1.98 cm³ of 1.0 M aqueous TBA solution is added. After 3 hours stirring, twice in a two-hour period, 1.98 cm³ of 1.0 M aqueous TBA solution are added. The precipitated solids are filtered after four days. The filtrate is allowed to stand and the product precipitated in the next three days is filtered. Thus 1.44 g (26%) of product are obtained (HPLC purity: 99.84%). Powder X-ray diffractogram of the product is depicted in FIG. 1. Powder X-ray diffraction positions and relative intensities are summarized in Table 1.

Preparation of Amorphous Rosuvastatin TBA Salt [Compound of the Formula (III)]

Example 53

0.35 g (0.69 mmol) of rosuvastatin TBA salt prepared according to the method of Example 42 were dissolved in 2.5 cm³ of methanol at 25° C. The solution thus obtained is evaporated to dryness in vacuo. The residue is dried until the next day in air at 25° C. Thus 0.33 g (94%) of amorphous product having the powder X-ray diffractogram shown in FIG. 2 are obtained.

Example 54

3.0 g (6 mmol) of crystalline Form II rosuvastatin methylester are dissolved in 12 cm³ of methanol at 25° C. and while stirring, 5.9 cm³ of 1.0 M aqueous TBA solution are added. Thereafter five times in two-hour periods, further 1.2 cm³ of 1.0 M aqueous TBA solution are added to the reaction mixture. After further stirring for 24 hours, the mixture is evaporated. Thus 3.20 g (96%) of amorphous product are obtained.

Preparation of Rosuvastatin Calcium Salt [Compound of the Formula (IV)] from Rosuvastatin TBA Salt [Compound of the Formula (III)]

Example 55

1.67 g (3.0 mmol) of amorphous rosuvastatin TBA salt are added to a two-layer mixture of 10 cm³ of water and 15 cm³ of ethylacetate at room temperature while stirring thoroughly. After all the solids are dissolved, in 15-minutes periods, five times 5×1.5 cm³ (5×7.5 mmol) of saturated calcium chloride solution are added to the two-layered mixture dropwise. After the addition, the reaction mixture is stirred for a further hour at room temperature and the upper ethylacetate layer is separated, washed with 5 cm³ of 2.0 M calcium chloride solution and twice with 5 ml water each. Removal of water from the organic layer is carried out by azeotropic distillation by evaporating the ethylacetate layer to dryness and the thus obtained residue is dissolved in 5 cm³ dry ethylacetate. The solution is stirred for 5 minutes and evaporated to dryness in vacuo at 42-45° C. at 50 mbar pressure. The residue is mixed with 6 cm³ dry cyclohexane and the suspension is stirred for 30 minutes. The solids are filtered, washed with 5 cm³ of dry cyclohexane and dried in vacuo at 50° C. for 7 hours. Thus 1.30 g (87%) of product are obtained.

Example 56

1.67 g (3.0 mmol) of rosuvastatin TBA salt are added to a biphasic mixture of 10 cm³ of water and 15 cm³ of ethylacetate at room temperature while stirring intensely. After the solids are dissolved, in 15-minute periods, 3×0.4 g (3×2.5 mmol) of solid calcium acetate are added to the biphasic mixture. After the addition, the reaction mixture is stirred for a further hour at room temperature, the upper ethylacetate layer is separated and washed with 3×5 cm³ of water. The organic layer is dried by azeotropic distillation by evaporating the ethylacetate layer in vacuo to dryness. The thus obtained white residue is dissolved in 5 cm³ of dry ethylacetate. The solution is stirred for 5 minutes and evaporated at 42-45° C. in vacuo at the pressure of 50 mbar. The residue is mixed with 6 cm³ of dry cyclohexane and the suspension is stirred for 30 minutes. The solids are filtered, washed with 5 cm³ of dry cyclohexane and dried in vacuo at 50° C. for 7 hours. After drying, 1.36 g (91%) of product are obtained.

Preparation of Rosuvastatin Zinc Salt [Compound of the Formula (V)] from Rosuvastatin TBA Salt [Compound of the Formula (III)]

Example 57

In a light-protected apparatus, 27.0 g (0.049 mol) of amorphous rosuvastatin TBA salt are dissolved in 1620 cm³ of distilled water at a temperature between 20 and 25° C. The solution is filtered and subsequently the solution of 9.59 g (0.053 mol) of $ZnSO_4H_2O$ prepared in 80 cm³ of distilled water are added at a temperature between 20 and 25° C. dropwise. The suspension is cooled to a temperature between 5 and 10° C., filtered and washed with 100 cm³ of distilled water. Thereafter the thus obtained wet product weighing 59.9 g is suspended in 540 cm³ of distilled water in argon atmosphere at a temperature between 5 and 10° C. for 41 hours. The solids are filtered, washed with distilled water and dried in vacuo. Thus 33.1 g (80%) of title product are obtained.

Example 58

In a light-protected apparatus, 1.16 g (0.002 mol) of amorphous rosuvastatin TBA salt are added to a mixture of 11.7 cm³ of ethylacetate and 55 cm³ of distilled water while stirring. Thereafter in an argon atmosphere, 1.27 cm³ of aqueous 2.23 M $ZnSO_4$ solution are added dropwise at a temperature between 20 and 25° C. while stirring. After one hours stirring, the layers are separated and the organic layer is washed with 2×1.3 cm³ of 2.23 M aqueous $ZnSO_4$ solution, followed by 1.3 cm³ of water. The organic layer is evaporated and after adding ethylacetate repeatedly, the residues of water is removed by azeotropic distillation. The suspension thus obtained is cooled, filtered, washed with 2 cm³ of ethylacetate and dried in vacuo. The thus obtained 0.70 g (0.0007 mol) product is stirred in a solution consisting of 0.76 mg of sodium hydroxide dissolved in 8.2 cm³ of distilled water in a stream of argon for four hours at 25° C. The mixture is filtered and the wet product is suspended repeatedly in 8.2 cm³ of alkaline solution having the same composition as mentioned above for further two hours in argon atmosphere. The solids are filtered, washed with 2 cm³ of alkaline solution having the same composition and dried in vacuo protected from light. Thus 0.53 g (76%) of title product are obtained.

Example 59

In an apparatus protected from light, 6.15 g (0.011 mol) of rosuvastatin TBA salt are dissolved in 370 cm$^3$ of distilled water at a temperature between 20 and 25° C. Thereafter in an argon atmosphere, the solution of 2.15 g (0.012 mol) $ZnSO_4H_2O$ in 17.8 cm$^3$ of distilled water are added dropwise at a temperature of 20 to 25° C. The suspension is cooled to a temperature between 5 to 10° C., filtered and washed with 30 cm$^3$ of distilled water. Thereafter the we product is stirred in 123 cm$^3$ of distilled water in an argon atmosphere at a temperature between 5 and 10° C. for 41 hours. After filtration the solids are washed with 4×25 cm$^3$ of distilled water and dried in vacuo protected from light. Thus 4.60 g (81%) of title compound are obtained.

Example 60

In an apparatus protected from light, 6.20 g (0.0112 mol) of rosuvastatin TBA salt are dissolved in 370 cm$^3$ distilled water at a temperature between 20 to 25° C. Thereafter in argon atmosphere, the solution of 2.20 g (0.0122 mol) of $ZnSO_4H_2O$ in 17.8 cm$^3$ of distilled water are added dropwise at a temperature between 20 and 25° C. The suspension is cooled to a temperature between 5 and 10° C., filtered and washed with 30 cm$^3$ of distilled water. Thereafter the wet product is stirred in 125 cm$^3$ of distilled water in argon atmosphere at a temperature between 5 and 10° C. for 41 hours. After filtration, the solids are washed with 3×30 cm$^3$ of distilled water and dried in vacuo protected from light. Thus 4.80 g (84%) of title product are obtained.

Example 61

In an apparatus protected from light, 1.20 g (0.0022 mol) of rosuvastatin TBA salt are dissolved in 72 cm$^3$ of distilled water at a temperature between 20 and 25° C. Thereafter in argon atmosphere, the solution of 0.53 g (0.003 mol) $ZnSO_4H_2O$ in 4.4 cm$^3$ of distilled water are added to the reaction mixture at a temperature between 20 and 25° C. The suspension is cooled to a temperature between 5 and 10° C. and filtered and washed with 5 cm$^3$ of distilled water. Subsequently the wet product is stirred in 25 cm$^3$ of distilled water in argon atmosphere at a temperature between 5 and 10° C. for 41 hours. After filtration, the solids are washed with 3×5 cm$^3$ of distilled water and dried in vacuo protected from light. Thus 0.86 g (79%) of title product are obtained.

Example 62

In an apparatus protected from light, 7.50 g (0.014 mol) of rosuvastatin TBA salt are dissolved in 450 cm$^3$ of distilled water at a temperature between 20 and 25° C. Subsequently in an argon atmosphere, the solution of 2.70 g (0.015 mol) $ZnSO_4H_2O$ prepared with 22.6 cm$^3$ of distilled water are added dropwise at a temperature between 20 and 25° C. Thereafter the suspension is cooled to a temperature between 5 and 10° C., filtered and the solids are washed with 30 cm$^3$ of distilled water. The wet product weighing 13.8 g are stirred in 150 cm$^3$ of distilled water in argon atmosphere at a temperature between 5 to 10° C. for 41 hours. After filtration, the solids are washed with 3×30 cm$^3$ of distilled water and dried in vacuo protected from light. Thus 5.95 g (86%) of title product are obtained.

Example 63

In an apparatus protected from light, 3.50 g (0.006 mol) of rosuvastatin TBA salt are dissolved in 210 cm$^3$ of distilled water at a temperature between 20 and 25° C. Subsequently in an argon atmosphere, the solution of 1.54 g (0.008 mol) $ZnSO_4H_2O$ prepared in 13 cm$^3$ of distilled water are added dropwise at a temperature between 20 and 25° C. The suspension is cooled to a temperature between 5 and 10° C., filtered and the solids are washed with 15 cm$^3$ of distilled water. Thereafter the wet product weighing 6.50 g is stirred in 110 cm$^3$ of distilled water in argon atmosphere at a temperature between 5 and 10° C. for 41 hours. After filtration, the solids are washed with 3×20 cm$^3$ of distilled water and dried in vacuo protected from light. Thus 2.65 g (82%) of title product are obtained.

Example 64

In an apparatus protected from light, 2.90 g (0.005 mol) of rosuvastatin TBA salt are dissolved in 175 cm$^3$ of distilled water at a temperature between 20 and 25° C. Thereafter in argon atmosphere, the solution of 1.28 g (0.0068 mol) $ZnSO_4H_2O$ in 11 cm$^3$ of distilled water are added dropwise at a temperature between 20 and 25° C. The suspension is cooled to a temperature between 5 and 10° C., filtered and washed with 10 cm$^3$ of distilled water. Thereafter the wet product weighing 5.40 g is stirred in 85 cm$^3$ of distilled water in argon atmosphere at a temperature between 5 and 10° C. for 41 hours. After filtration washed with 3×20 cm$^3$ of distilled water and dried in vacuo protected from light. Thus 2.30 g (86%) of title product are obtained.

Preparation of Rosuvastatin Zinc Salt [Compound of the Formula (V)] from Crystalline Form II Rosuvastatin Methylester [Compound of the Formula (IIa)]

Example 65

2.0 g (4.0 mmol) of crystalline Form II rosuvastatin methylester are dissolved in 8 cm$^3$ of methanol at 25° C. and while stirring, at the same temperature, 4 cm$^3$ of 1.0 M aqueous TBA solution are added. Five times in two-hour periods further 0.8 cm$^3$ of 1.0 M aqueous TBA solution are added to the reaction mixture. The mixture is stirred for further 24 hours, evaporated and 20 cm$^3$ of ethylacetate and 6 cm$^3$ of distilled water are added to the residue. Into the biphasic mixture, 2.2 cm$^3$ of 2.2 M aqueous $ZnSO_4$ solution are added dropwise in ten minutes at a temperature between 20 and 25° C. After 1 hour stirring, the layers are separated and the organic layer is washed with 2×10 cm$^3$ of 2.2 M aqueous $ZnSO_4$ solution and 10 cm$^3$ of distilled water. The organic layer is evaporated and after adding ethylacetate repeatedly, the residual water is removed by azeotropic distillation. The suspension thus obtained is cooled, filtered, washed with 2 cm$^3$ of ethylacetate and dried in vacuo. Thus 1.24 g (60%) crude product are obtained, which is stirred in an aqueous solution consisting of 0.8 mg of sodium hydroxide and 8 cm$^3$ of distilled water in argon atmosphere at a temperature between 0 and 5° C. for 36 hours. Thereafter the mixture is filtered, the solids are washed with 2 cm$^3$ of alkaline water having the same composition as described above and dried in vacuo protected from light. Thus 1.10 g (89%) of title product are obtained.

Example 66

3.0 g (6.0 mmol) of crystalline Form II rosuvastatin methylester are dissolved in 12 cm$^3$ of methanol at 25° C. and while stirring, 5.9 cm³ of 1.0 M aqueous TBA solution are added at the same temperature. Thereafter five times in two-hour periods further 1.2 cm³ of 1.0 M aqueous TBA solution are added to the reaction mixture. The mixture is stirred for further 24 hours, evaporated and by adding 3×40 cm³ eof ethylacetate, the residual water is removed by repeating azeotropic distillation three times. Into the residue thus obtained 34 cm³ of ethylacetate and 10 cm³ of distilled water are added. Subsequently 3.7 cm³ of 2.2 M aqueous ZnSO₄ solution are added into the biphasic mixture in ten minutes at a temperature between 20 and 25° C. After one hour stirring, the layers are separated, the organic layer is washed with 2×10 cm³ of 2.2 M aqueous ZnSO₄ solution and 10 cm³ of distilled water. The organic layer is evaporated and the remaining water is removed by repeated azeotropic distillation using ethylacetate. The suspension is cooled, filtered, washed with 3 cm³ of ethylacetate and dried in vacuo. Thus 2.50 g (81%) of crude product are obtained, which are stirred in the solution of 1.2 mg of sodium hydroxide in 12 cm³ of distilled water in an argon atmosphere for 36 hours at a temperature between 0 and 5° C. The mixture is filtered, washed with alkaline water having the same composition as described above and dried in vacuo protected from light. Thus 2.25 g (90%) of title product are obtained.

Figure 1:
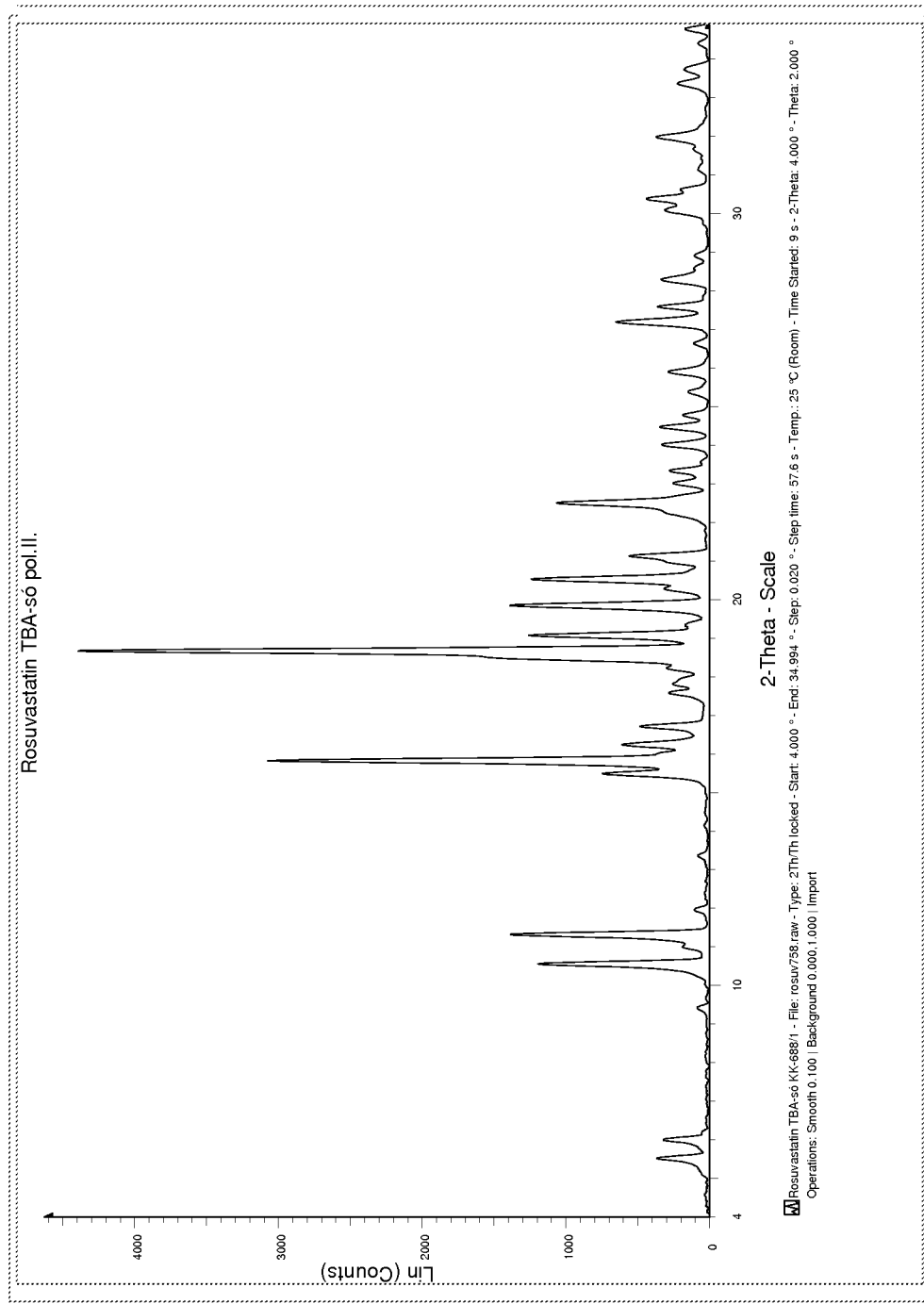
FIG. 1 Illustrates the powder X-ray diffractogram of crystalline Form II rosuvastatin TBA salt [compound of the Formula (III)]
Figure 2:
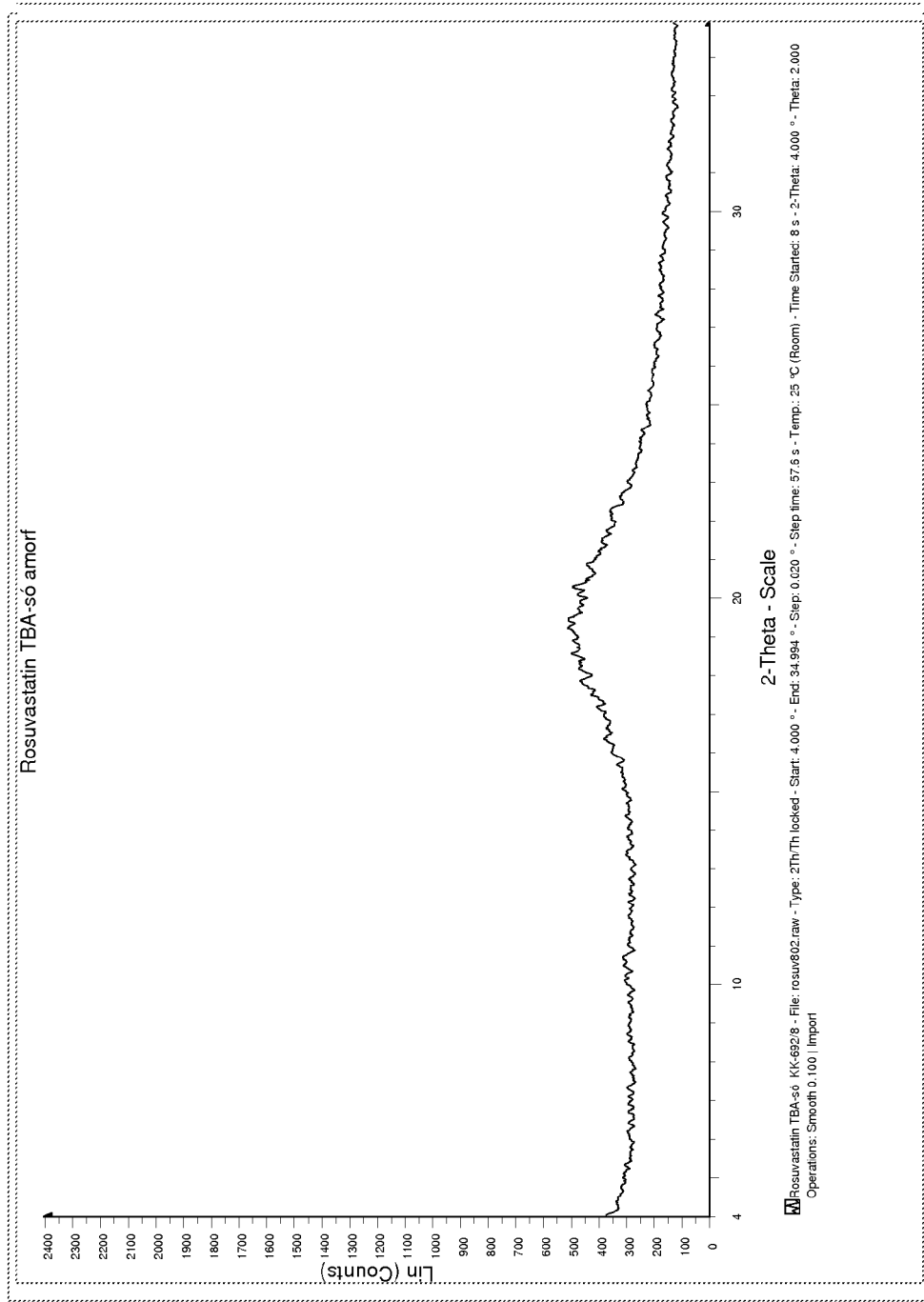
FIG. 2 Illustrates the powder X-ray diffractogram of amorphous rosuvastatin TBA salt [compound of the Formula (III)]
Figure 3:
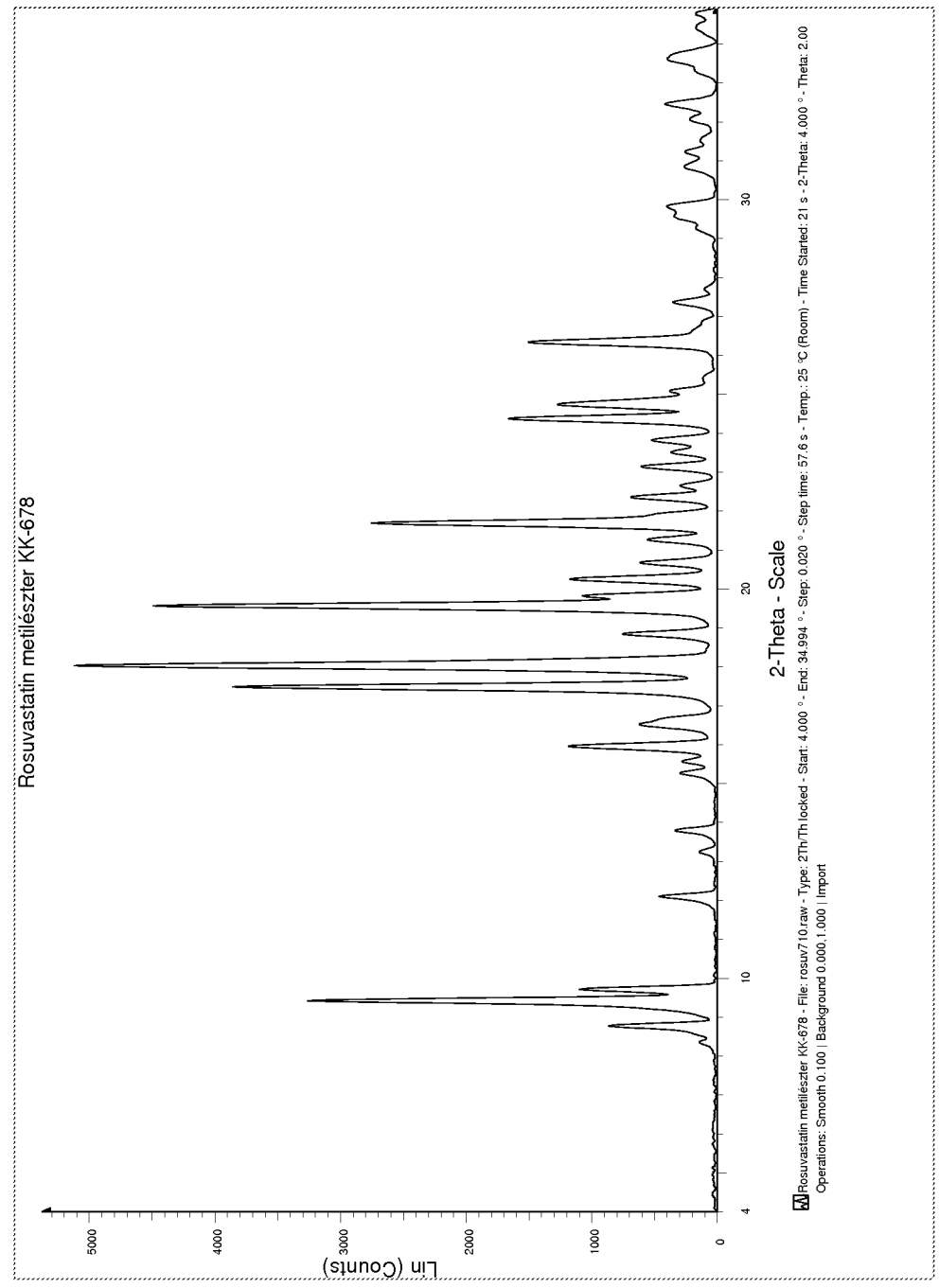
FIG. 3 Illustrates the powder X-ray diffractogram of crystalline Form II rosuvastatin methylester [compound of the Formula (IIa)]
Figure 4:
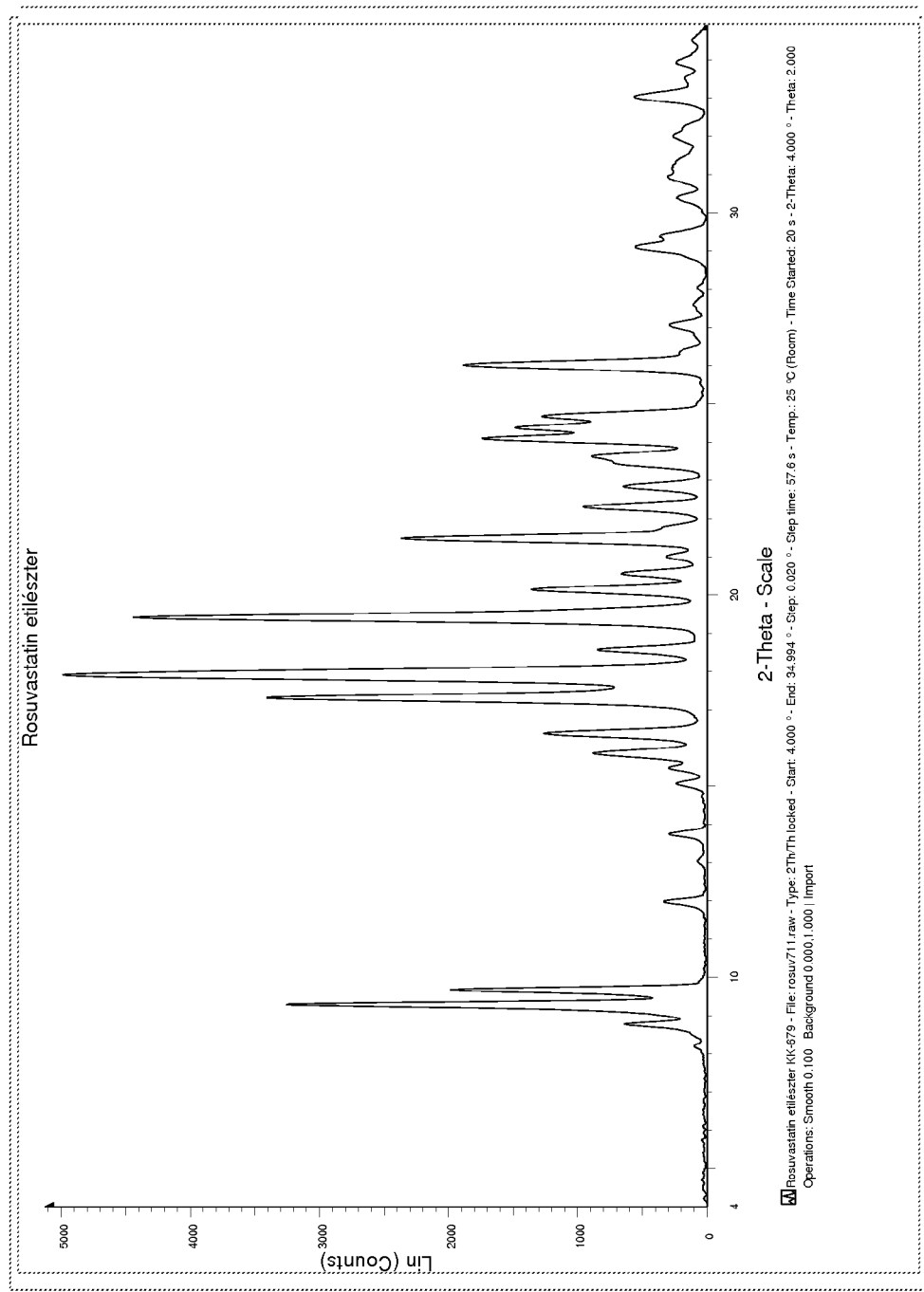
FIG. 4 Illustrates the powder X-ray diffractogram of crystalline Form II rosuvastatin ethylester [compound of the Formula (IIb)]

What we claim is:

1. A method for the preparation of a rosuvastatin product, which method is one of the following methods I or II:

I) for the preparation of rosuvastatin TBA salt of Formula (III)

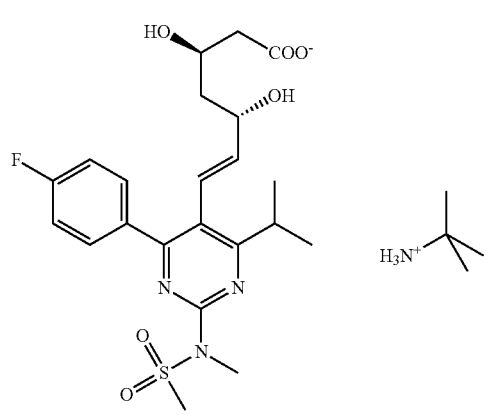

which comprises reacting a rosuvastatin ester of Formula (II)

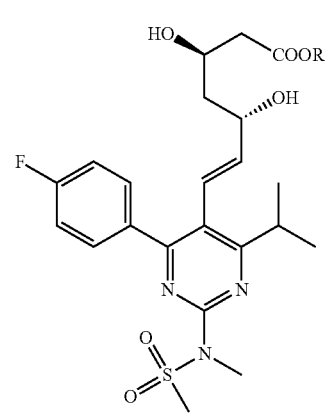

wherein

R represents methyl, ethyl or tert-butyl, in a polar solvent with 1.5 to 5 molar equivalents of tert-butylamine in aqueous solution at a temperature between 10° C. and the boiling point of the solvent;

or

II) for the preparation of crystalline Form II rosuvastatin TBA salt of Formula (III), which comprises suspending a rosuvastatin ester of Formula (II), wherein R represents methyl, ethyl or tert-butyl,

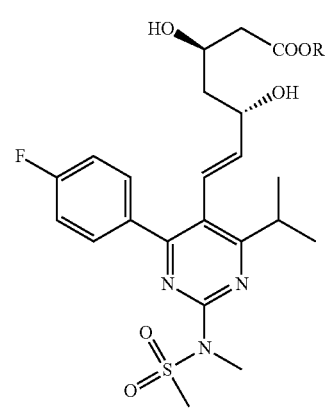

in water, adding an aqueous solution of equimolar amount of tert-butylamine at a temperature between 10 and 50° C., optionally repeating the addition of tert-butylamine within 2 to 24 hours one to five times by adding the aqueous solution of 0.1 to 0.5 molar equivalents of tert-butylamine each time, removing the separated solids from the solution after 72 to 96 hours and isolating the thus obtained crystalline Form II rosuvastatin TBA salt of Formula (III).

2. A method according to claim 1, which is a method II for the preparation of crystalline Form II rosuvastatin TBA salt of Formula (III).

3. A method according to claim 1, which method is one of the methods I or II, wherein the starting material is crystalline Form II rosuvastatin methylester of Formula (IIa)

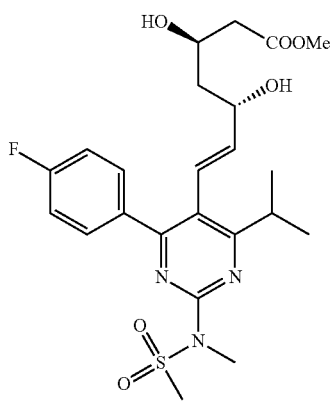

crystalline Form II rosuvastatin ethylester of Formula (IIb)

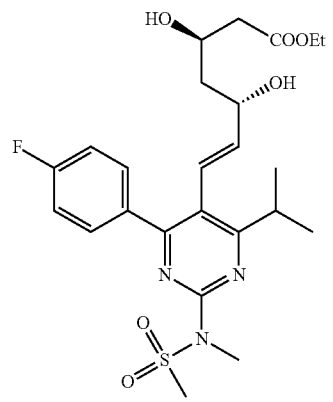

or rosuvastatin-tert-butylester of Formula (IIc)

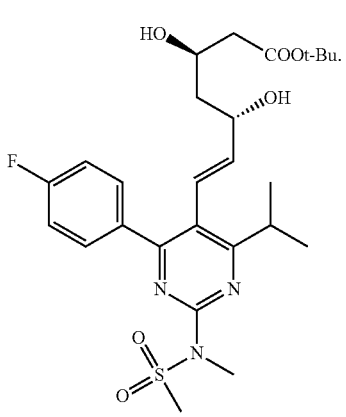

4. A method for preparing a rosuvastatin calcium (2:1) salt, which includes a reaction involving a rosuvastatin TBA salt of Formula (III) prepared according to claim 1, which method is method I.

5. A method for preparing a rosuvastatin zinc (2:1) salt, which includes a reaction involving a rosuvastatin TBA salt of Formula (III) prepared according to claim 1, which method is method I.

6. A method according to claim 1, which is a method I for the preparation of rosuvastatin TBA salt of Formula (III).

7. A method according to claim 2, wherein the rosuvastatin ester of Formula (II) is crystalline and is of Formula (IIb)

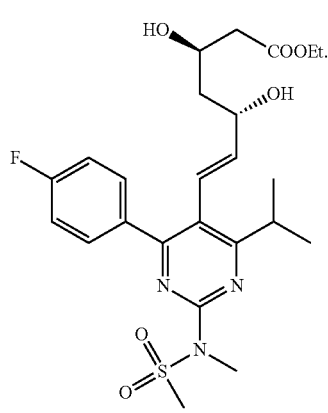

8. A method according to claim 2, wherein the adding of an aqueous solution of equimolar amount of tert-butylamine is at a temperature of 25° C.

9. A method according to claim 2, wherein the addition of tert-butylamine within 2 to 24 hours is repeated one to five times.

10. A method according to claim 2, wherein the addition of tert-butylamine within 2 to 24 hours is repeated one to five times by adding the aqueous solution of 0.2 molar equivalents of tert-butylamine each time.

11. A method according to claim 6, wherein the rosuvastatin ester of Formula (II) has a solid crystalline form.

12. A method according to claim 6, wherein the polar solvent is water, methanol or acetonitrile.

13. A method according to claim 6, wherein the polar solvent is acetonitrile.

14. A method according to claim 6, wherein the reaction is with 2.0 molar equivalents of tert-butylamine.

15. A method according to claim 1, which method is method I, wherein the starting material is crystalline Form II rosuvastatin methylester of Formula (IIa)

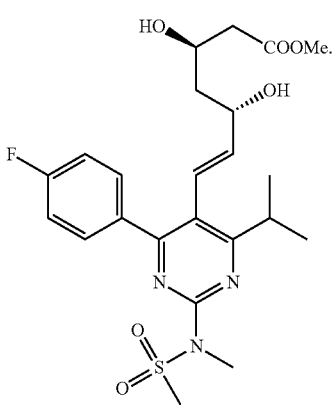

16. A method according to claim 1, which method is method I, wherein the starting material is crystalline Form II rosuvastatin ethylester of Formula (IIb)

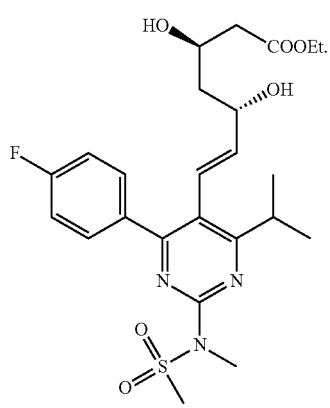

(IIb)

17. A method according to claim 1, which method is method I, wherein the starting material is rosuvastatin-tert-butylester of Formula (IIc)

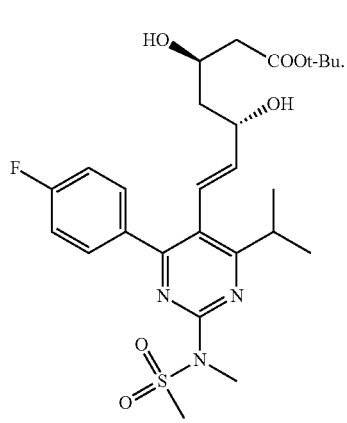

(IIc)

18. A method according to claim 1, which method is method II, wherein the starting material is crystalline Form II rosuvastatin methylester of Formula (IIa)

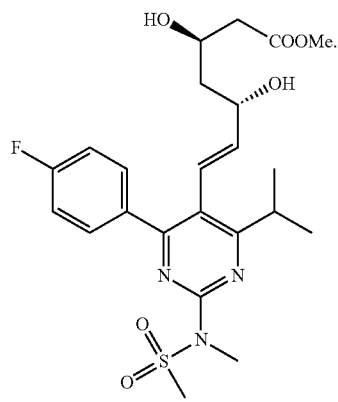

(IIa)

19. A method according to claim 1, which method is method II, wherein the starting material is crystalline Form II rosuvastatin ethylester of Formula (IIb)

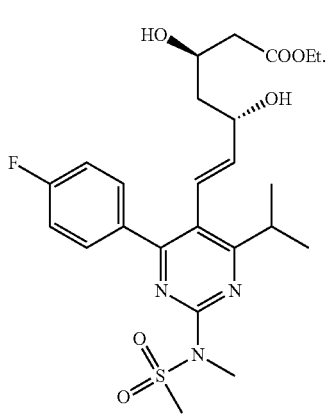

(IIb)

20. A method according to claim 1, which method is method II, wherein the starting material is rosuvastatin-tert-butylester of Formula (IIc)

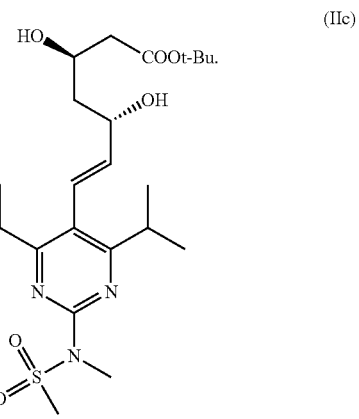

(IIc)

21. A method for preparing a rosuvastatin calcium (2:1) salt, which includes a reaction involving a rosuvastatin TBA salt of Formula (III) prepared according to claim 1, which method is method II.

22. A method for preparing a rosuvastatin zinc (2:1) salt, which includes a reaction involving a rosuvastatin TBA salt of Formula (III) prepared according to claim 1, which method is method II.

23. A method according to claim 4, wherein the rosuvastatin ester of Formula (II) has a solid crystalline form.

24. A method according to claim 5, wherein the rosuvastatin ester of Formula (II) has a solid crystalline form.

25. A method according to claim 21, wherein the rosuvastatin ester of Formula (II) is crystalline and is of Formula (IIb)
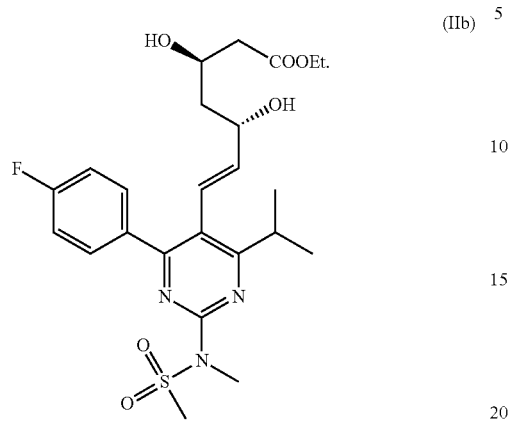
26. A method according to claim 22, wherein the rosuvastatin ester of Formula (II) is crystalline and is of Formula (IIb)
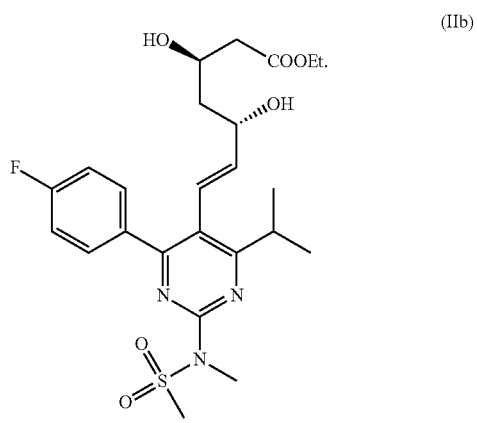 [SMILES: COC(=O)C[C@H](O)C[C@H](O)/C=C/c1c(-c2ccc(F)cc2)nc(N(C)S(C)(=O)=O)nc1C(C)C]
* * * * *